United States Patent
Deutsch

(10) Patent No.: US 9,943,651 B2
(45) Date of Patent: Apr. 17, 2018

(54) PRESSURE REGULATING SYRINGE AND METHOD THEREFOR

(71) Applicant: Hospitech Respiration Ltd., Petach-Tikva (IL)

(72) Inventor: Israel Deutsch, Petach-Tikva (IL)

(73) Assignee: Hospitech Respiration Ltd., Petach-Tikva (IL)

(*) Notice: Subject to any disclaimer, the term of this patent is extended or adjusted under 35 U.S.C. 154(b) by 894 days.

(21) Appl. No.: 14/350,821

(22) PCT Filed: Sep. 30, 2012

(86) PCT No.: PCT/IB2012/001920
§ 371 (c)(1),
(2) Date: Apr. 10, 2014

(87) PCT Pub. No.: WO2013/054165
PCT Pub. Date: Apr. 18, 2013

(65) Prior Publication Data
US 2014/0288408 A1    Sep. 25, 2014

Related U.S. Application Data

(60) Provisional application No. 61/545,600, filed on Oct. 11, 2011.

(51) Int. Cl.
*G01L 27/00* (2006.01)
*A61M 16/04* (2006.01)
(Continued)

(52) U.S. Cl.
CPC ............. *A61M 5/5086* (2013.01); *A61B 5/08* (2013.01); *A61M 5/31511* (2013.01);
(Continued)

(58) Field of Classification Search
CPC .. A61M 16/044; A61M 16/0434; A61M 5/48; A61M 5/482; A61M 5/484;
(Continued)

(56) References Cited

U.S. PATENT DOCUMENTS 3,895,668 A * 7/1975 Tangorra ................. B60B 21/02
152/379.3
4,370,982 A    2/1983 Reilly
(Continued)

FOREIGN PATENT DOCUMENTS

| CN | 2822547 | 10/2006 |
|---|---|---|
| CN | 101874909 | 11/2010 |

(Continued)

OTHER PUBLICATIONS

Decision of Rejection dated Sep. 30, 2016 From the Japanese Patent Office Re. Application No. 2014-535175 and Its Translation Into English.
(Continued)

*Primary Examiner* — Michael Tsai

(57) ABSTRACT

A pressure regulating syringe comprises a barrel assembly terminating with a tubular tip positionable in fluid communication with a fluid chamber, a plunger that is manually and axially displaceable within a barrel of the barrel assembly, a pressure sensor mounted onto the plunger adjacent to its distal end, for generating one or more electrical signals representative of a change in pressure within the fluid chamber, circuitry housed within the plunger for processing the generated signals, and a display mounted on the plunger for displaying an output indicative of the processed signals. The output is changeable upon axial displacement of the plunger when the tubular tip is positioned in fluid communication with the fluid chamber, which is for example a cuff surrounding a medical tube. Fluid is delivered by manually manipulating a fluid delivery element in response to the
(Continued)

displayed output until a desired fluid delivery operation is performed.

26 Claims, 18 Drawing Sheets

(51) Int. Cl.
| | |
|---|---|
| *A61M 5/50* | (2006.01) |
| *A61M 5/48* | (2006.01) |
| *A61M 25/10* | (2013.01) |
| *A61M 16/00* | (2006.01) |
| *A61B 5/08* | (2006.01) |
| *A61M 5/315* | (2006.01) |
| *A61M 5/31* | (2006.01) |

(52) U.S. Cl.
CPC ........ *A61M 5/486* (2013.01); *A61M 16/0003* (2014.02); *A61M 16/021* (2017.08); *A61M 16/044* (2013.01); *A61M 25/10* (2013.01); *A61M 25/10182* (2013.11); *G01L 27/002* (2013.01); *A61M 5/31505* (2013.01); *A61M 25/10188* (2013.11); *A61M 2005/3125* (2013.01); *A61M 2016/0027* (2013.01); *A61M 2205/583* (2013.01); *A61M 2205/70* (2013.01); *A61M 2205/8206* (2013.01)

(58) Field of Classification Search
CPC .................. A61M 5/486; A61M 5/488; A61M 2016/0027; A61M 2025/0001; A61M 2025/0002; A61M 2025/0003; A61M 25/1018; A61M 25/10181; A61M 25/10182; A61M 25/10184; A61M 25/10187; A61M 25/10188; A61M 2205/0227; G01L 27/00; G01L 27/002
USPC ........................................ 73/1.62, 1.68, 1.63
See application file for complete search history.

(56) References Cited

U.S. PATENT DOCUMENTS

| | | | |
|---|---|---|---|
| 4,655,749 A | 4/1987 | Fischione | |
| 4,723,938 A | 2/1988 | Goodin et al. | |
| 4,743,230 A | 5/1988 | Nordquest | |
| 4,758,223 A | 7/1988 | Rydell | |
| 4,815,313 A * | 3/1989 | Beard .................. | A61B 5/03 |
| | | | 73/1.62 |
| 4,872,483 A | 10/1989 | Shah | |
| 4,919,121 A | 4/1990 | Rydell et al. | |
| 5,004,472 A | 4/1991 | Wallace | |
| 5,019,041 A | 5/1991 | Robinson et al. | |
| 5,135,488 A | 8/1992 | Foote et al. | |
| 5,137,514 A | 8/1992 | Ryan | |
| 5,163,904 A | 11/1992 | Lampropoulos et al. | |
| 5,213,115 A | 5/1993 | Zytkovicz et al. | |
| 5,215,523 A | 6/1993 | Williams et al. | |
| 5,259,838 A | 11/1993 | Taylor et al. | |
| 5,270,685 A | 12/1993 | Hagen et al. | |
| 5,273,537 A | 12/1993 | Haskvitz et al. | |
| 5,279,563 A | 1/1994 | Brucker et al. | |
| 5,284,480 A | 2/1994 | Porter et al. | |
| 5,306,248 A | 4/1994 | Barrington | |
| 5,472,424 A | 12/1995 | Lampropoulos et al. | |
| 5,656,772 A | 8/1997 | Markel | |
| 5,685,851 A | 11/1997 | Murphy et al. | |
| 5,701,904 A | 12/1997 | Simmons et al. | |
| 5,713,242 A | 2/1998 | Kanner et al. | |
| 5,800,344 A | 9/1998 | Wood, Sr. et al. | |
| 5,808,203 A | 9/1998 | Nolan, Jr. et al. | |
| 6,063,057 A | 5/2000 | Choh | |
| 6,120,457 A * | 9/2000 | Coombes .......... | A61B 5/02156 |
| | | | 600/486 |
| 6,139,523 A | 10/2000 | Taylor et al. | |
| 6,179,815 B1 | 1/2001 | Foote | |
| 6,254,569 B1 | 7/2001 | O'Donnell et al. | |
| 6,354,993 B1 | 3/2002 | Kaplan et al. | |
| 6,394,977 B1 | 5/2002 | Taylor et al. | |
| 6,706,069 B2 | 3/2004 | Berger | |
| 6,796,959 B2 | 9/2004 | Davis et al. | |
| 6,890,298 B2 | 5/2005 | Berci et al. | |
| 7,018,359 B2 * | 3/2006 | Igarashi .............. | A61M 16/044 |
| | | | 128/205.23 |
| 7,044,909 B2 | 5/2006 | Berci et al. | |
| 7,273,053 B2 | 9/2007 | Zocca et al. | |
| 7,291,131 B2 | 11/2007 | Call | |
| D562,447 S | 2/2008 | Call et al. | |
| 7,530,970 B2 | 5/2009 | McArthur et al. | |
| 7,892,202 B2 | 2/2011 | Lampropoulos et al. | |
| 7,927,270 B2 | 4/2011 | Dlugos et al. | |
| 7,946,981 B1 | 5/2011 | Cubb | |
| 7,955,301 B1 | 6/2011 | McKay | |
| 7,959,607 B2 | 6/2011 | Smit et al. | |
| 8,029,440 B2 | 10/2011 | Birnkrant et al. | |
| 8,118,776 B2 | 2/2012 | Lampropoulos et al. | |
| 8,187,180 B2 | 5/2012 | Pacey | |
| 8,291,768 B2 | 10/2012 | Spiegel et al. | |
| 8,388,524 B2 | 3/2013 | Bullard | |
| 8,397,577 B2 | 3/2013 | Slocum, Sr. et al. | |
| 8,460,230 B2 | 6/2013 | Perry et al. | |
| 2001/0014768 A1 | 8/2001 | Kaplan et al. | |
| 2003/0000526 A1 * | 1/2003 | Gobel ............... | A61M 16/0452 |
| | | | 128/204.18 |
| 2003/0088156 A1 | 5/2003 | Berci et al. | |
| 2003/0205089 A1 * | 11/2003 | Nelson .................. | G01L 9/0073 |
| | | | 73/715 |
| 2004/0260238 A1 | 12/2004 | Call | |
| 2005/0004518 A1 * | 1/2005 | Call ...................... | A61M 5/486 |
| | | | 604/97.02 |
| 2005/0049556 A1 | 3/2005 | Tanaka | |
| 2005/0148821 A1 | 7/2005 | Berci et al. | |
| 2005/0244801 A1 | 11/2005 | DeSalvo | |
| 2006/0276693 A1 | 12/2006 | Pacey | |
| 2007/0173697 A1 | 7/2007 | Dutcher et al. | |
| 2007/0179342 A1 | 8/2007 | Miller et al. | |
| 2008/0140338 A1 | 6/2008 | No et al. | |
| 2008/0249370 A1 | 10/2008 | Birnkrant et al. | |
| 2009/0157040 A1 * | 6/2009 | Jacobson .......... | A61M 5/16804 |
| | | | 604/505 |
| 2009/0227947 A1 | 9/2009 | Caclin | |
| 2010/0069851 A1 | 3/2010 | Vad et al. | |
| 2010/0179488 A1 * | 7/2010 | Spiegel .............. | A61M 16/044 |
| | | | 604/240 |
| 2010/0224187 A1 | 9/2010 | Dalton | |
| 2010/0252048 A1 * | 10/2010 | Young .................. | A61M 16/044 |
| | | | 128/207.15 |
| 2011/0092773 A1 | 4/2011 | Goldstein | |
| 2011/0178372 A1 | 7/2011 | Pacey et al. | |
| 2011/0245609 A1 | 10/2011 | Laser | |
| 2011/0270027 A1 | 11/2011 | Augarten et al. | |
| 2011/0270038 A1 | 11/2011 | Jiang et al. | |
| 2012/0078055 A1 | 3/2012 | Berci et al. | |
| 2012/0095294 A1 | 4/2012 | McGrath et al. | |
| 2012/0123194 A1 | 5/2012 | Beckman et al. | |
| 2012/0204884 A1 | 8/2012 | Howard | |
| 2012/0215069 A1 | 8/2012 | Bullard | |
| 2012/0312100 A1 | 12/2012 | Slocum | |
| 2012/0316460 A1 | 12/2012 | Stout | |
| 2013/0018227 A1 | 1/2013 | Schoonbaert | |
| 2013/0019689 A1 | 1/2013 | Slocum et al. | |
| 2013/0057667 A1 | 3/2013 | McGrath | |
| 2013/0060090 A1 | 3/2013 | McGrath et al. | |

FOREIGN PATENT DOCUMENTS

| | | |
|---|---|---|
| CN | 202859210 | 4/2013 |
| EP | 0316763 | 5/1989 |
| EP | 0396353 | 11/1990 |
| EP | 0964713 | 12/1999 |
| EP | 1949875 | 7/2008 |
| EP | 2218473 | 8/2010 |

(56) References Cited

FOREIGN PATENT DOCUMENTS

| GB | 2348607 | 10/2000 |
|----|---------|---------|
| GB | 2452776 | 3/2009 |
| IE | 58056 | 6/1993 |
| JP | 02-001525 | 1/1990 |
| JP | 2002-507733 | 3/2002 |
| JP | 2006-097670 | 4/2006 |
| JP | 2010-538723 | 12/2010 |
| WO | WO 92/15361 | 9/1992 |
| WO | WO 99/33508 | 7/1999 |
| WO | WO 99/48551 | 9/1999 |
| WO | WO 2004/075954 | 9/2004 |
| WO | WO 2009/037447 | 3/2009 |
| WO | WO 2010/052275 | 5/2010 |
| WO | WO 2012/094403 | 7/2012 |
| WO | WO 2012/155056 | 11/2012 |

OTHER PUBLICATIONS

Communication Pursuant to Article 94(3) EPC Dated Jun. 8, 2016 From the European Patent Office Re. Application No. 12840717.8.
International Search Report and the Written Opinion dated Feb. 14, 2013 From the International Searching Authority Re. Application No. PCT/IB2012/001920.
Notification of Office Action and Search Report dated May 25, 2015 From the State Intellectual Property Office of the People's Republic of China Re. Application No. 201280050272.1 and Its Translation Into English.
Supplementary European Search Report and the European Search Opinion dated May 21, 2015 From the European Patent Office Re. Application No. 12840717.8.
International Preliminary Report on Patentability dated Apr. 24, 2014 From the International Searching Authority Re. Application No. PCT/IB2012/001920.
Notice of Reason for Rejection dated Nov. 13, 2015 From the Japanese Patent Office Re. Application No. 2014-535175 and Its Translation Into English.
Notice of Reason for Rejection dated Oct. 27, 2017 From the Japan Patent Office Re. Application No. 2017-12638 and Its Translation Into English. (8 Pages).
Office Action dated Jun. 20, 2017 From the Israel Patent Office Re. Application No. 232086 and Its Translation Into English. (10 Pages).
Communication Pursuant to Article 94(3) EPC dated Jan. 26, 2018 From the European Patent Office Re. Application No. 12840717.8. (7 Pages).

\* cited by examiner

PRESSURE REGULATING SYRINGE AND METHOD THEREFOR

RELATED APPLICATIONS

This application is a National Phase of PCT Patent Application No. PCT/IB2012/001920 having International filing date of Sep. 30, 2012, which claims the benefit of priority under 35 USC § 119(e) of U.S. Provisional Patent Application No. 61/545,600 filed on Oct. 11, 2011.The contents of the above applications are all incorporated by reference as if fully set forth herein in their entirety.

FIELD OF THE INVENTION

The present invention relates to the field of syringes. More particularly, the invention relates to a syringe for regulating, measuring, and analyzing the pressure in a cuff surrounding a medical tube.

BACKGROUND OF THE INVENTION

An endotracheal tube (ETT), which provides an open airway to the patient's lungs, is inserted into the patient's trachea, in a process known as intubation. A balloon-like cuff near the distal end of the ETT, and in communication with a thin conduit embedded within the ETT wall, is inflated within the trachea and prevents leaks around the ETT.

After intubating a patient and setting the ventilation parameters, the physician inflates the cuff by a syringe and checks for leakage by means of an imprecise osculating stethoscope. The cuff is generally inflated to a pressure between 20 and 30 cm $H_2O$, while ensuring that the Intra-Cuff Pressure (ICP) will not exceed 40 cm $H_2O$ to prevent damage to the tracheal tissue. An overinflated cuff during prolonged intubation is liable to damage the tracheal mucosa, including mucosal tracheal stenosis, ulceration, fistula, and granulomas. It is also important that the cuff is sufficiently inflated to adequately seal against the tracheal wall and to prevent aspiration of secretions and gastric influx which are liable to lead to ventilator-associated pneumonia (VAP).

A common prior art technique for measuring the ICP is by means of an analog indicator placed in fluid communication with the interior of the syringe barrel. However, the syringe barrel interior volume varies while the ICP is being regulated, and therefore the pressure reading is not accurate since the instantaneous volume of the barrel and of the connection assembly needs to be known in order to derive the ICP.

Another prior art method for measuring the ICP is by attaching a digital manometer to the inlet valve of the cuff. However, manometers are bulky and expensive devices that are not always available. The most common manometers are small battery powered devices, using one or more pressure sensors and simple circuitry to provide the required pressure. However, manometers require the connection of a conduit that reduces, when in use, the pressure within the cuff due to the additional conduit volume, therefore reducing the accuracy of the reading.

Battery or AC-powered pressure regulators are also used for measuring the ICP by means of a microcontroller, pump and valves to enable continuous control of a preset pressure. Since these devices are of a significant volume and weight, they cannot be connected directly to the ETT check valve and require additional conduit and installation procedures. Their high cost limit wide use thereof.

Another prior art device for measuring or regulating the ICP comprises an inflator bulb for manually pumping air into the cuff, e.g. the Posey Cufflator™ manufactured by the Posey Company, Arcadia, Calif. Since the cuff is in fluid communication with the inflator bulb, the ICP tends to vary while the device is attached due to the added volume of the bulb and during slow detachment of the device from the ETT, causing unintentional flow of air and a pressure inaccuracy. As a result of its considerable cost, such a prior art device is reused, leading to cross contamination and infection of intubated patients.

The medical staff is directed to routinely monitor the ICP while the patient is intubated, for example once a shift, ensuring that it continues to be within the acceptable pressure range which is indicative of proper tracheal sealing. However, due to an overload of the medical staff, particularly in an Intensive Care Unit (ICU), due to a lack of expensive ICP pressure measuring devices, or due to difficult to manipulate or inaccurate devices, this standard of care is many times not followed.

U.S. Patent Application Publication No. 2010/0179488 discloses a syringe having an internal pressure sensor comprises a syringe barrel; a piston within the barrel; a spring coupled to the piston at a first position of the spring, the spring having a second portion that is movable in response to fluid pressure within a syringe cavity; and a pressure sensor having an indicator correlated to a plurality of positions of the second portion of the spring to indicate a pressure of a fluid. The spring can be a bellows. The fluid chamber can be in fluid communication with an endotracheal tube cuff.

A considerable force has to be applied to the plunger during distal displacement in order to counteract the spring force and the sliding friction between the seal and the barrel. Another drawback of this prior art syringe is that it comprises a pressure indicator that is moveable with respect to the barrel, and therefore has to be constantly calibrated due to a changing resistance force in order to ensure accurate readings.

Pressure indicating syringes for use in other medical procedures are disclosed in EP 0589439, GB 1568283, IE 922955, WO 82/03553, WO 82/03555, WO 87/01598, WO 92/07609, WO 93/01573, U.S. Pat. Nos. 4,064,879, 4,710, 172, 4,759,750, 5,163,904, 5,259,838, 5,270,685, 5,295,967, 5,449,344, 5,722,955, and US 2004/0254533.

It is an object of the present invention to provide a syringe for accurately measuring the ICP.

It is an additional object of the present invention to provide a relatively inexpensive syringe for regulating, and providing accurate readings of, the ICP while inflating or deflating the cuff surrounding a medical tube.

It is an additional object of the present invention to provide a syringe for simultaneously regulating the ICP and indicating the volume of gas added to, or removed from, a cuff during a pressure regulating operation.

It is an additional object of the present invention to provide a sufficiently inexpensive pressure regulating syringe that is disposable so as to prevent cross contamination and infection of patients.

It is an additional object of the present invention to provide a pressure regulating syringe that is operable with no more manual force that is needed by conventional syringes.

It is an additional object of the present invention to provide a pressure regulating syringe that is one time calibratable.

It is yet an additional object of the present invention to provide a pressure regulating syringe that can be connected to the check valve of a medical tube without requiring additional installation procedures.

Other objects and advantages of the invention will become apparent as the description proceeds.

SUMMARY OF THE INVENTION

The present invention provides a pressure regulating syringe, comprising a barrel assembly terminating with a tubular tip positionable in fluid communication with a fluid chamber, a plunger that is manually and axially displaceable within a barrel of said barrel assembly, a pressure sensor mounted onto said plunger adjacent to a distal end thereof, for generating one or more electrical signals representative of a change in pressure within said fluid chamber, circuitry housed within said plunger for processing said generated signals, and a display mounted on said plunger for displaying an output indicative of said processed signals, wherein said output is changeable upon axial displacement of said plunger when said tubular tip is positioned in fluid communication with said fluid chamber.

In one aspect, the plunger comprises a distally disposed piston fitted with sealing means for sealingly engaging an inner surface of the barrel, said piston being formed with a central opening by which the pressure sensor is in fluid communication with the barrel assembly tip and the displayed output being a pressure reading.

In one aspect, the sensor is a differential pressure sensor having a first pressure port in fluid communication with the barrel assembly tip and a second pressure port in fluid communication with ambient pressure air flowing through a clearance between the plunger and the barrel assembly and through void regions of the plunger, the processing circuitry adapted to compute and to transmit to the display a pressure differential between the pressure of the fluid chamber and ambient pressure.

In one aspect, the ambient pressure is a calibrated value.

In one aspect, the syringe further comprises a proximally disposed control button in electrical communication with a battery and processor, for initiating a pressure measuring mode when momentarily depressed.

In one aspect, a calibrating mode for outputting the calibrated value to the display is initiated when the control button is depressed longer than a predetermined period of time and the barrel assembly tip is in fluid communication with ambient pressure air.

In one aspect, the calibrating mode is suppressed when the pressure differential is greater than a predetermined value.

In one aspect, the plunger is axially displaceable to regulate the volume of a barrel interior between the sealing means and the barrel assembly tip and the pressure of the fluid chamber, until a desired pressure reading is displayed.

In one aspect, the plunger is releasably securable to the barrel assembly after the desired pressure differential reading is displayed.

In one aspect, the differential pressure sensor is a piezoelectric pressure sensor.

In one aspect, the fluid chamber is a cuff surrounding an endotracheal tube, said cuff being normally isolated from ambient pressure air by means of a check valve and having a pressure that is regulatable during axial displacement of the plunger when the syringe is coupled to a tube surrounding said check valve and the barrel assembly tip presses and displaces a piston of said check valve.

In one aspect, the differential pressure sensor comprises two absolute pressure sensors configured such that the first pressure port is associated with a first absolute pressure sensor and the second pressure port is associated with a second absolute pressure sensor.

In one aspect, the circuitry is operable in an analysis mode during which the generated signals are analyzed in a frequency or time domain. The circuitry may be set to a dormant state during operation of the analysis mode or of a pressure measuring mode and then set to an active state in response to a wakeup event.

In the prior art, the ICP is regulated by a trial and error process whereby the pressure is monitored by a manometer or any other gauge, and a syringe is manipulated by a number of operations until after a number of attempts the desired pressure is achieved.

The present invention in contrast is directed to a method for delivering pressurized fluid, comprising the steps of providing a syringe comprising a barrel assembly terminating with a tubular tip, a plunger that is axially displaceable within a barrel of said barrel assembly, a pressure sensor for generating electrical signals which is mounted onto said plunger adjacent to a distal end thereof, circuitry housed within said plunger for processing said generated signals, and a display mounted on said plunger for displaying an output indicative of said processed signals; positioning said tip in fluid communication with a fluid chamber; initiating a pressure measuring mode whereby said electrical signals being representative of a change in pressure within said fluid chamber are generated and an output associated with said signals is displayed on said display, and manually manipulating a fluid delivery element in response to said displayed output until a desired fluid delivery operation is performed.

In one aspect, the displayed output is a pressure level in the fluid chamber.

In one aspect, the distal tip of the syringe is positioned in fluid communication with the fluid chamber by being placed in actuating relation with a valve which is in fluid communication with the fluid chamber and the plunger is manipulated in order to regulate the pressure in the fluid chamber.

In one aspect, the pressurized fluid is delivered to a cuff surrounding a medical tube, said medical tube being selected from the group consisting of an endrotracheal tube, a tracheotomy tube, a laryngeal mask airway tube, a cannula, and a catheter.

In one aspect, the plunger is manipulated in order to inflate a tire.

In one aspect, the fluid chamber is the epidural space located within the spinal canal, and the epidural space is identified by securing a needle to the distal tip of the syringe and causing said needle to penetrate the vertebral bone until a decrease in pressure indicative of penetration into the epidural space is displayed, whereupon medication is injected into the epidural space via said needle.

In one aspect, the pressurized fluid is delivered to a bleeding injury site at less than the systolic pressure in order to stop a wounded blood vessel from bleeding.

In one aspect, the displayed output is a spectral analysis derived output of the generated signals.

In one aspect, the fluid delivery element is a ventilator and the spectral analysis derived output provides an indication of a current respiratory state of a patient suffering from non-synchronized breathing and requiring assisted ventilation.

In one aspect, an indication is provided in the analysis mode whether a cuff surrounding a medical tube ruptured or whether a conduit for inflating said cuff is occluded.

The syringe of the present invention provides at least the following advantages:

1. It simultaneously measures and regulates the ICP.
2. It provides an accurate digital reading of the ICP, which is immediately displayable.
3. It is inexpensive.
4. It is user friendly.
5. It is light.
6. It can be manipulated by one hand, to both change a mode of operation and to regulate the ICP.
7. The instantaneous ICP can be maintained for extended periods of time.
8. It is dedicated for one patient use, being disposable and preventing cross infection between patients.

DETAILED DESCRIPTION OF PREFERRED EMBODIMENTS

The present invention is a compact and electronically controlled pressure regulating syringe that comprises a plunger in which is housed a pressure sensor and corresponding circuitry. The syringe is operable in four modes, as will be described hereinafter: (1) a pressure measuring mode, (2) a pressure adjustment mode, (3) a calibrating mode, and (4) an analysis mode. Despite its user friendly, precise, and reliable operability, the syringe is sufficiently inexpensive so as to be disposable.

The following description relates to a syringe that is adapted to regulate the pressure of a cuff surrounding an ETT. It will be appreciated that the pressure regulating syringe of the present invention is also operable in conjunction with other cuffed medical tubes, including a tracheotomy tube (TRT), laryngeal mask airway (LMA) tube, and a cuffed cannula or catheter.

Figure 1:
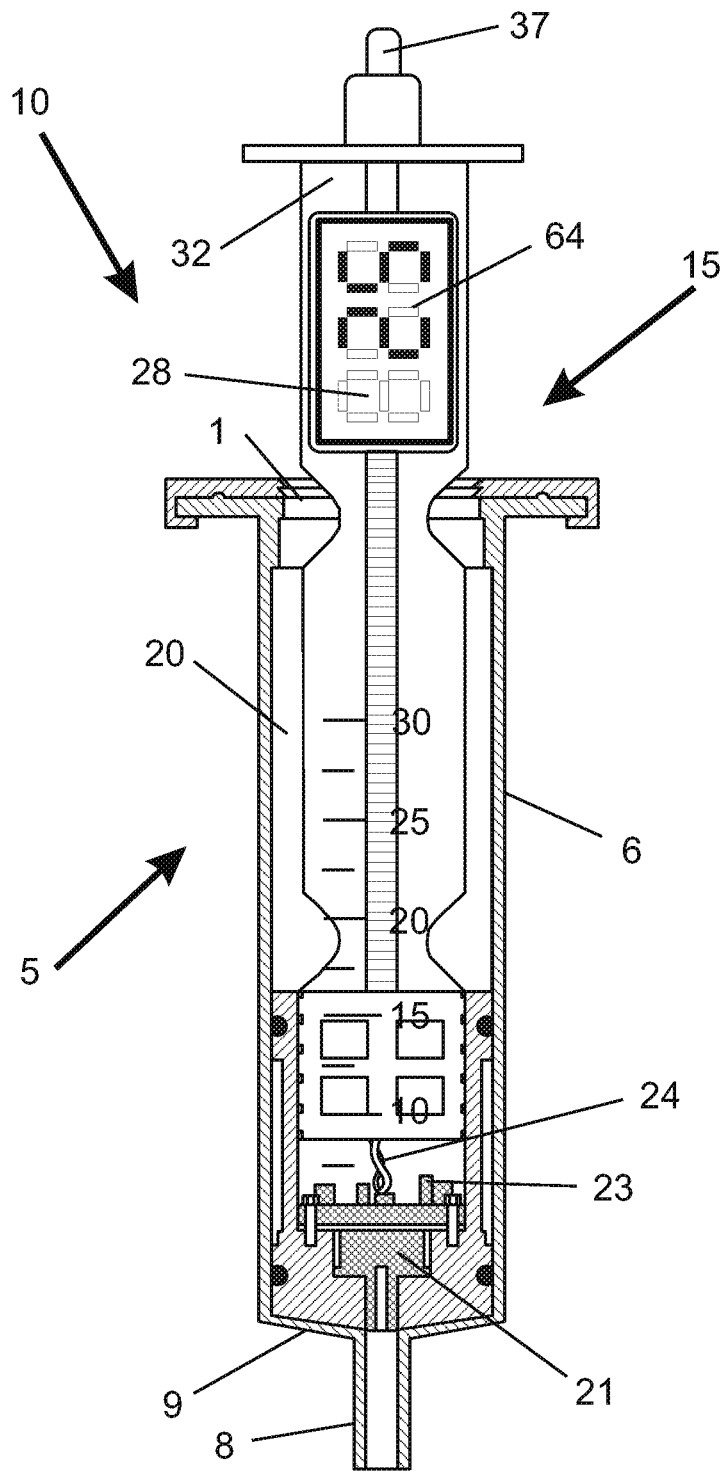
FIG. 1 is a front cross sectional view of a syringe according to one embodiment of the present invention, showing the plunger distally displaced to a fullest extent.

FIG. 1 illustrates a front cross sectional view of a syringe indicated, generally by numeral 10, according to one embodiment of the present invention.

Syringe 10 comprises barrel assembly 5 and plunger 15, which is manually displaceable within the interior of, and securable at a given relative position to, barrel 6 of barrel assembly 5. Barrel assembly 5 has a proximal opening 1 that has a larger diameter than that of the plunger main body, to permit displacement of plunger 15 without interference and to permit passage of ambient air along the radial clearance 20 between plunger 15 and barrel 6 for purposes of pressure measurement.

A differential pressure sensor 21 that transmits electrical signals in response to pressure measurements, e.g. a piezoelectric pressure sensor, is mounted adjacent to the distal end of plunger 15 and is in fluid communication with tubular syringe tip 8 extending distally from the distal end 9 of barrel 6 through which pressurized air is dischargeable to the cuff. The electrical signals after being amplified by means of circuitry 23 are transmitted via cables 24 embedded within plunger 15 to processing circuitry so that a pressure reading will be viewable on display 28, which is mounted on the proximal end 32 of plunger 15. A control button 37, e.g. a pushbutton, for initiating the different modes of operation is also mounted on the proximal end 32 of plunger 15. Even though amplifying and processing circuitry are housed within plunger 15, the plunger has the same dimensions and is proximally and distally displaceable with the same ease as a conventional plunger.

Syringe 10 is suitably configured to allow pressure sensor 21 to sense both the ICP and ambient pressure and to thereby display the differential pressure therebetween.

Figure 2:
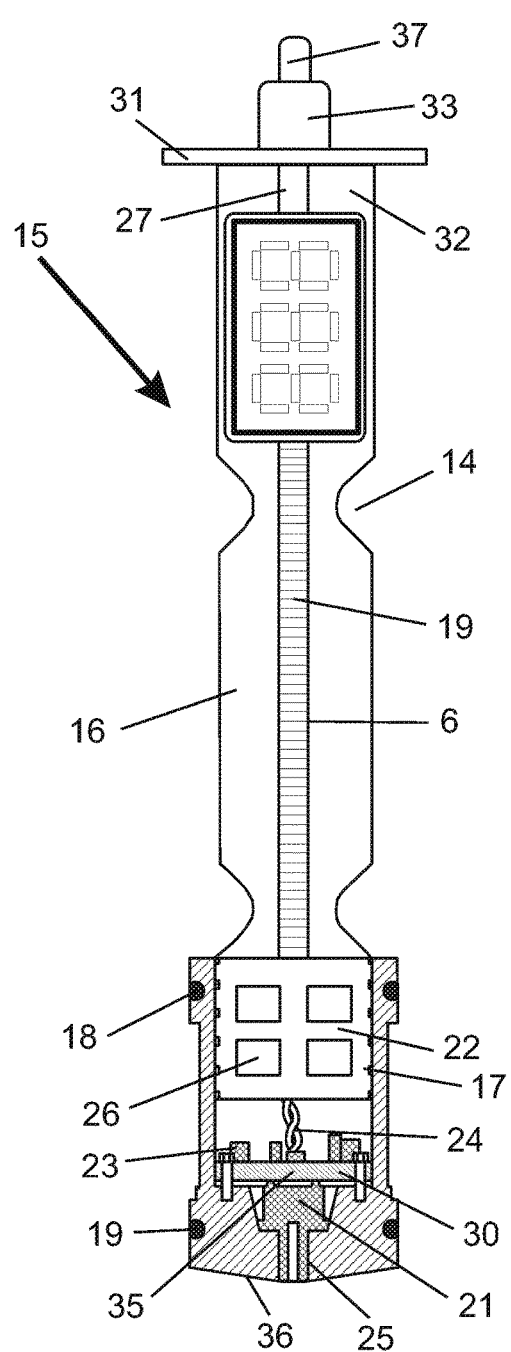
FIG. 2 is a front cross sectional view of a plunger when removed from the syringe of FIG. 1.
Figure 3:
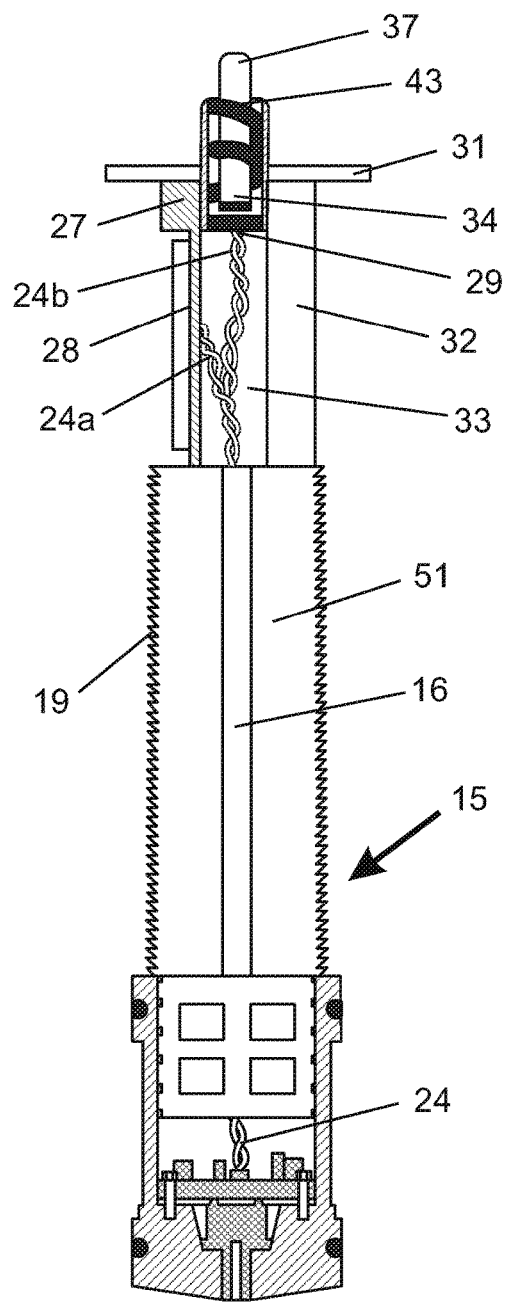
FIG. 3 is a side cross sectional view of the plunger of FIG. 2.

FIGS. 2 and 3 illustrate front and side views, respectively, of plunger 15 when removed from the barrel assembly. Plunger 15 comprises an elongated main body 16, which may be formed with regions 14 of reduced thickness for reduced material costs. Sawlike teeth 19 may be formed only on one or more limited circumferential and longitudinally extending regions of a member 51 radially protruding from main body 16 in order to be temporarily secured to the barrel assembly. Each circumferential region ranges from a few degrees to 45 degrees, or more, e.g. spanning an angle of 30 degrees, depending on the configuration of a locker ring 4 (FIGS. 10-11) with which a tooth bearing member 51 is engaged.

Cables 24 may be embedded within a central portion of main body 16 which is contiguous with each radially protruding member 21. Cable portions 24*a* and 24*b* branching from cable 24 extend through duct 33 vertically extending above each tooth bearing member 51 and are connected to display 28 and contact 29, respectively. Mounting plate 27 of an inverted L-shaped configuration, to the recessed vertical portion of which is mounted display 28, is attached to proximal end 32 of main body 16. Cable duct 33 protrudes through, and is perpendicular to, thin annular flange 31 which is mounted on top of mounting plate 27 and proximal end 32.

Cylindrical control button 37 is attached by means of spring 43 to cable duct 33. When control button 37 is depressed while flange 31, or any other portion of plunger 15, is held, electrically conducting portion 34 applied to the distal end of control button 37 makes an electrical connection with contact 29 mounted within cable duct 33 to initiate one of the modes of operation. Contact 29 is in electrical communication with the processing circuitry and battery, which are mounted within proximal end 32 or which are disposed at any other portion of plunger 15.

Plunger 15 has a hollowed elongated piston 17, within outer cavities of which are mounted two spaced thin and annular seal elements 18 and 19, respectively, for sealing engagement with the inner surface of the barrel. Abutment 22 extending distally from main body 16 is press fitted within a proximal portion of piston 17 adjacent to seal element 18. Hollowed portion 26 may be formed in abutment 22 to minimize usage of material, and to further allow passage of ambient pressure air from clearance 20 (FIG. 1) therethrough.

The interior of piston 17 is formed with a seat shaped complementarily to the shape of pressure sensor 21 and arranged such that ICP port 25 of sensor 21 extends proximally from distal edge 36 of piston 17 so as to be in fluid communication with the exterior of piston 17. Pressure sensor 21, amplifying circuitry 23, and cable 24 are connected to circuit board 30, which is attached to the interior of piston 17 at a region which is slightly proximal to seal element 19. Although not shown, an ambient pressure port of sensor 21 extends through pin 35 for connection to circuit board 30 and senses ambient pressure air flowing through abutment 22. Alternatively, the ambient pressure port may sense ambient pressure air flowing through recesses formed within the plunger body.

It will be appreciated that the circuitry for processing the signals generated by the pressure sensor can be configured in many different ways, such as by use of ASIC technology.

Figure 18:
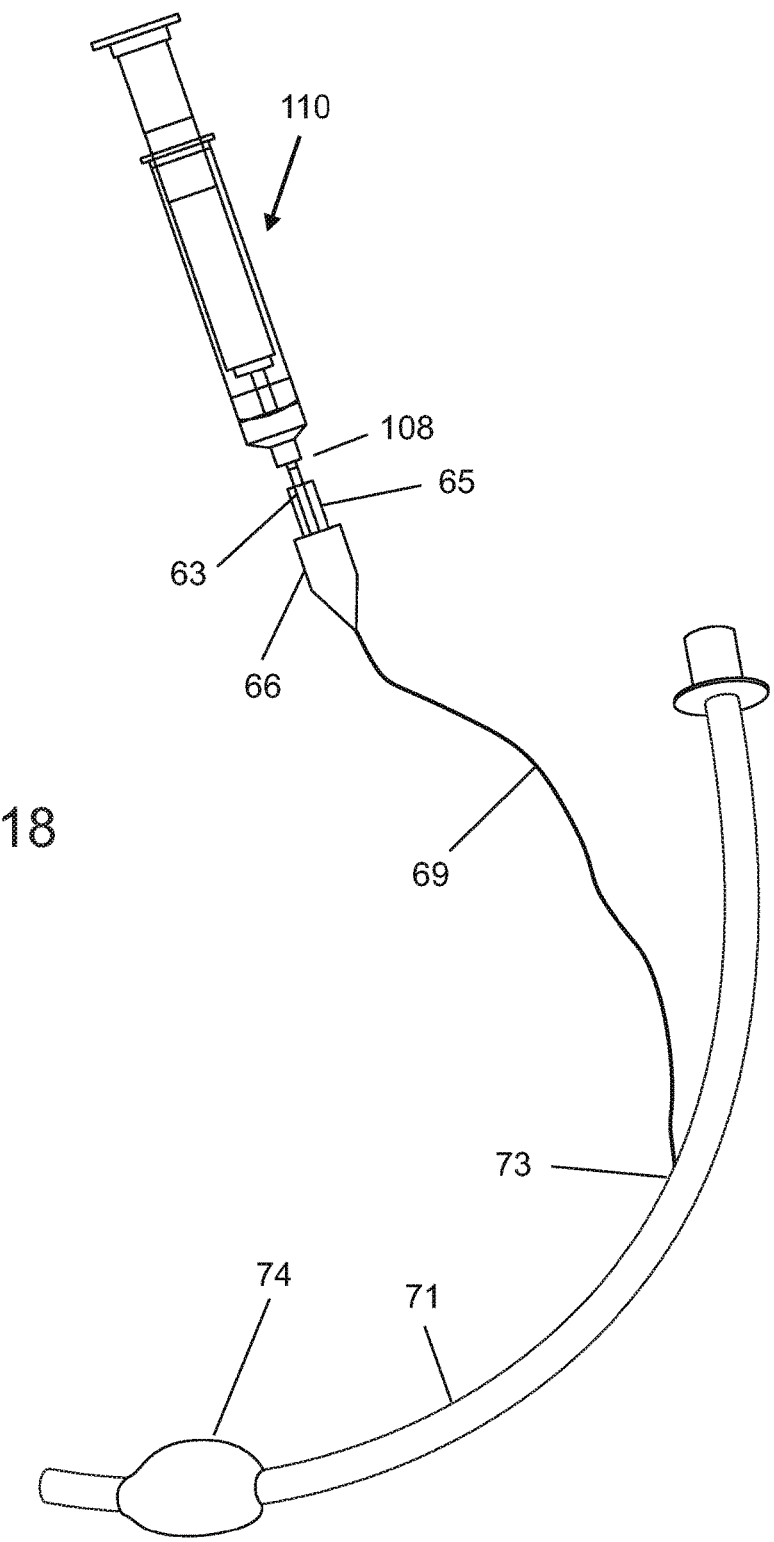
FIG. 18 is a front view of the syringe of FIG. 15 when coupled to a tube surrounding an ETT valve.

FIG. 18 illustrates a syringe 110 having an internally housed electronic pressure sensor while the syringe is coupled to a tube 63 surrounding ETT valve 65, which is e.g. a check valve or a poppet valve. Valve 65 is in fluid communication with pilot balloon 66 used for manual palpation to determine whether cuff 74 is adequately inflated, from which thin conduit 69 extends to ETT 71. Conduit 69, which is embedded within the wall of ETT 71 at contact point 73, extends to, and is in fluid communication with the interior of cuff 74, which surrounds ETT 71 at a distal region thereof. The syringe may have a volume, for example, of 10 cc, 20 cc, 30 cc, 50 cc, 100 cc, or 200 cc, or of any other desired volume.

Syringe tip 108 is configured to sufficiently press on the stem of valve 65, or to be in any other actuating relation therewith, when the syringe is coupled to tube 63, e.g. by means of a Luer lock or a slip tube, to cause displacement of the check valve. Thus the barrel interior of syringe 110, i.e. the variable volume for pressurizing air between the plunger and syringe tip 108, is in fluid communication with the interior of cuff 74 when the syringe is coupled with tube 63. Accordingly, displacement of the plunger, whether distally or proximally, will regulate the ICP. After cuff 74 achieves a desired pressure, the ICP may be retained by detaching syringe 110 from tube 63, causing valve 65 to return to its normally closed position. Tube 63 is of a minimal volume so as not to adversely affect the ICP when connected to the syringe.

The pressure sensor is mounted within the distal end of the plunger facing the barrel interior, and therefore its ICP port is also in fluid communication with cuff 74. As the pressure sensor is of the differential type, i.e. adapted to sense the difference in pressure between ambient pressure and the ICP, the pressure reading is independent of the instantaneous barrel volume and is therefore unmistakable.

Syringe 10 is shown in FIG. 1 to be operable in the pressure measuring mode while tip 8 is coupled to the tube surrounding the ETT valve and plunger 15 is distally displaced, and preferably set to an extreme distal position, in order to be optimally exposed to the ICP. An exemplary pressure reading of the ICP is indicated by indicia 64 of display 28.

During the pressure adjustment mode, the piston is displaced to an intermediate position within the barrel.

If the pressure reading is indicative of an excessive ICP, plunger 15 is simply proximally displaced to release via the check valve some of the air entrapped within the cuff until the pressure reading drops to a desired value.

Figure 4:
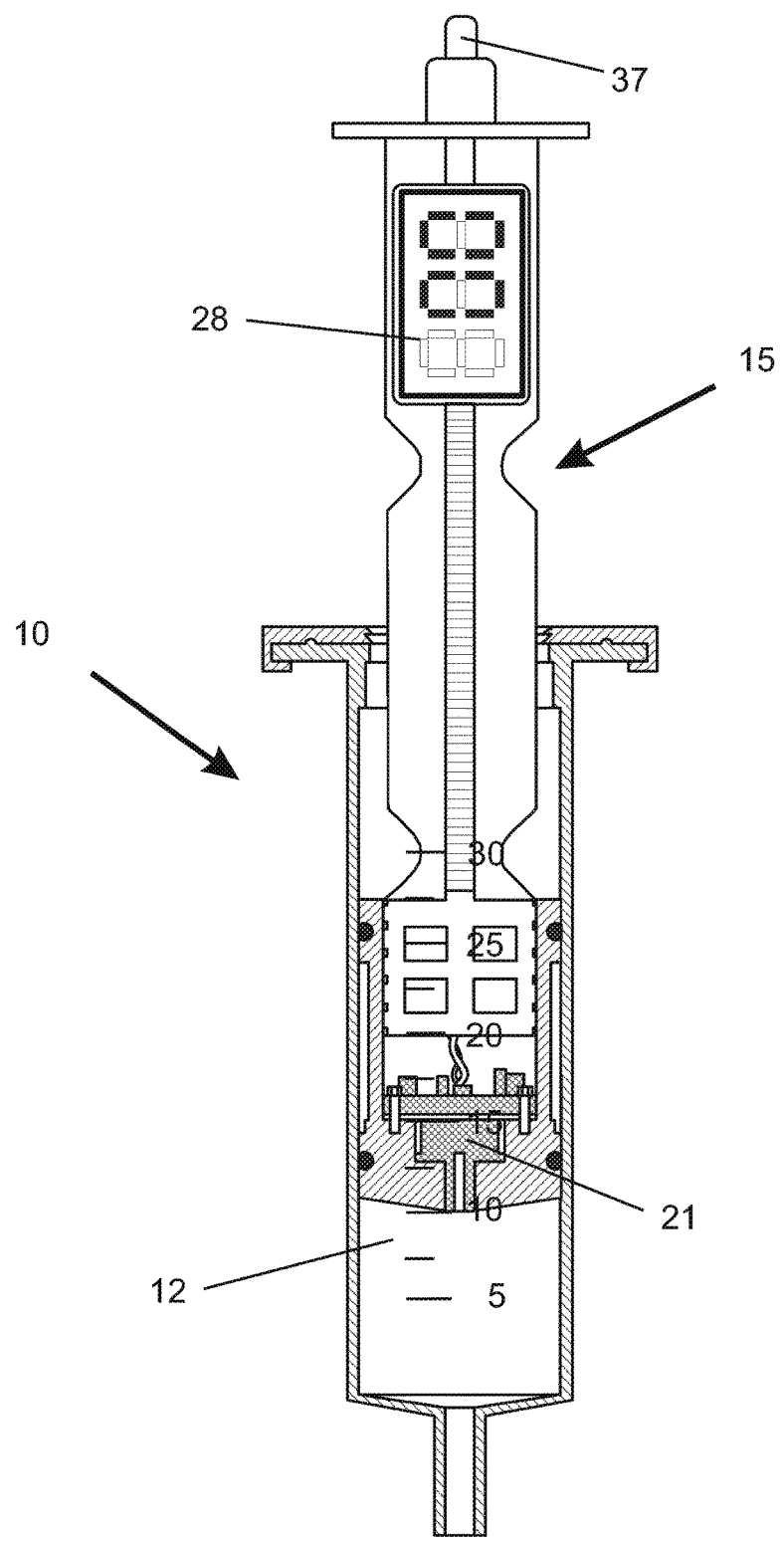
FIG. 4 is a front cross sectional view of the syringe of FIG. 1 when detached from a check valve tube.

The pressure adjustment mode may also be operational to increase the ICP. In order to admit a new charge of air into the barrel interior, syringe 10 has to be first detached from the valve tube. When plunger 15 is then detached from the barrel assembly, a new charge of air may be then admitted into barrel interior 12. Since syringe 10 has been detached from the valve tube, both pressure ports of pressure sensor 21 are exposed to atmospheric pressure and display 28 should indicate a differential pressure reading of 0, as shown in FIG. 4.

If for some reason display 28 does not indicate a differential pressure reading of 0, control button 37 is depressed in order to initiate the calibrating mode, whereby the display is zeroed.

Figure 5:
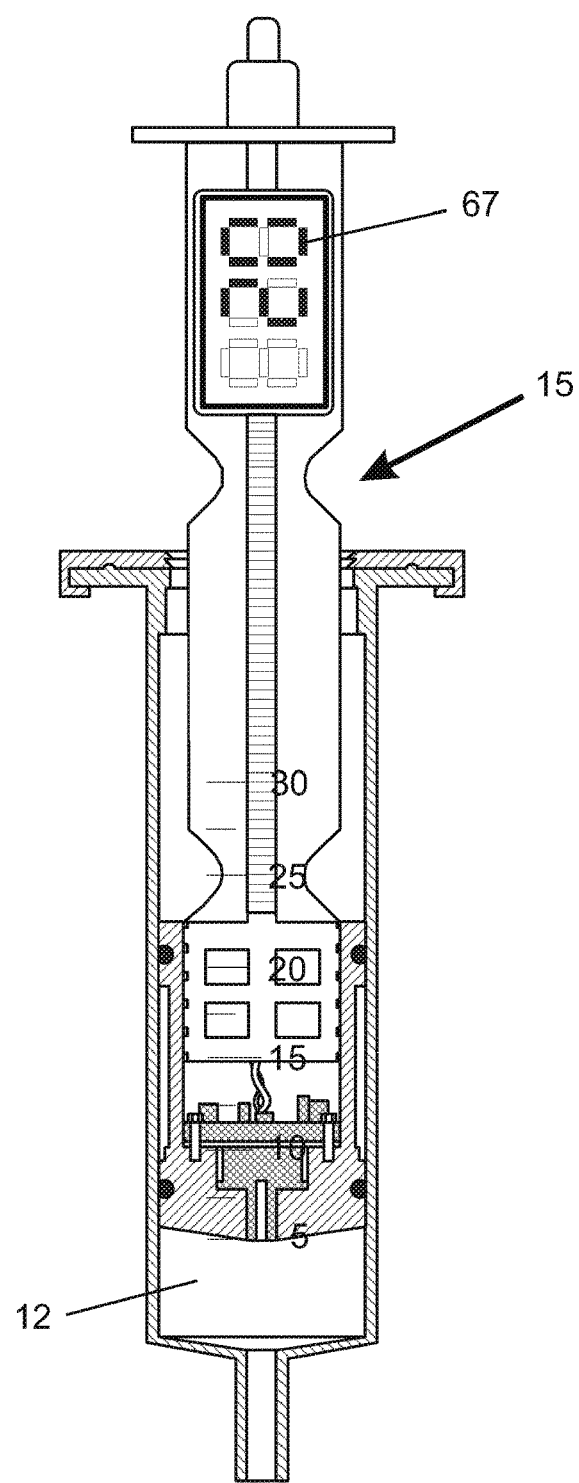
FIG. 5 is a front cross sectional view of the syringe of FIG. 1 when the plunger is distally displaced to achieve a desired differential pressure reading.

After the display is zeroed, plunger 15 is then distally displaced to reduce the volume of barrel interior 12 and to thereby increase the ICP, as shown in FIG. 5, until a desired differential pressure 67 is achieved and displayed. After the desired pressure has been achieved, a clinician monitors the pressure reading. If the pressure reading has changed, plunger 15 is displaced proximally or distally in response to the change in ICP that has to be made.

Figure 6:
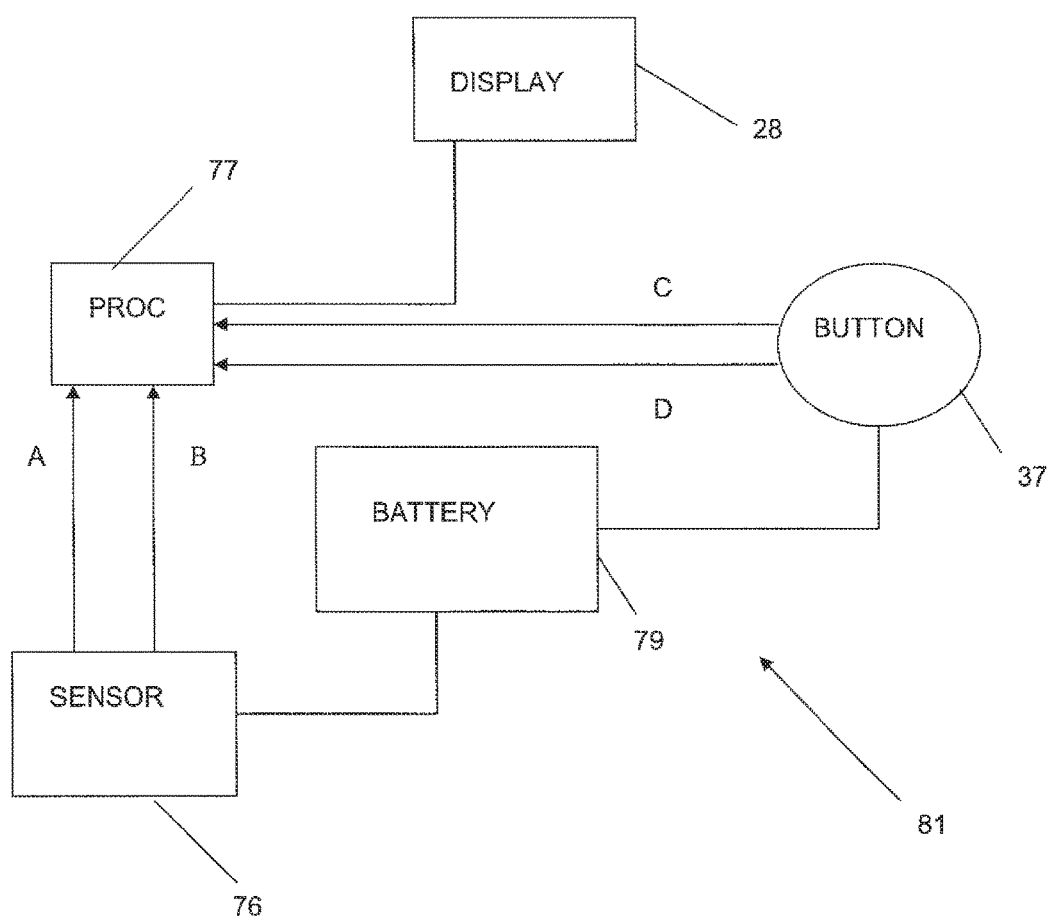
FIG. 6 is a block diagram of processing circuitry for outputting a pressure reading.

FIG. 6 illustrates a block diagram of the processing circuitry 81 for outputting a pressure reading. Processing circuitry 81 comprises pressure sensor 76, processor 77 for processing data generated by sensor 76, battery 79 for powering sensor 76 and processor 77, pressure reading display 28, and control button 37 for initiating a desired mode of operation.

When control button 37 is depressed to activate processing circuitry 81 and to initiate the pressure measuring mode, a signal C is transmitted to processor 77. Pressure sensor 76 then transmits signals A and B to processor 77, which are indicative of the absolute pressure at the ICP port and at the ambient pressure port, respectively. Processor 77 in response computes the difference between the pressure at the ICP port and at the ambient pressure port, and outputs the value of the computed differential pressure reading to display 28. The displayed indicia may blink if the power level of battery 79 is below a predetermined value.

Sensor 76 comprises two absolute pressure sensors configured such that the ICP port is associated with a first absolute pressure sensor and the ambient pressure port is associated with a second absolute pressure sensor, or alternatively sensor 76 is a differential pressure sensor transmitting a single signal to processor 77.

The calibrating mode is initiated when control button 37 is depressed for a predetermined period of time, e.g. 3 seconds. A signal D is transmitted to processor 77 after control button 37 is depressed for a sustained closure longer than the predetermined period of time, whereupon signals A and B are suppressed and a calibrated display of zero is indicated on display 28.

Figure 7:
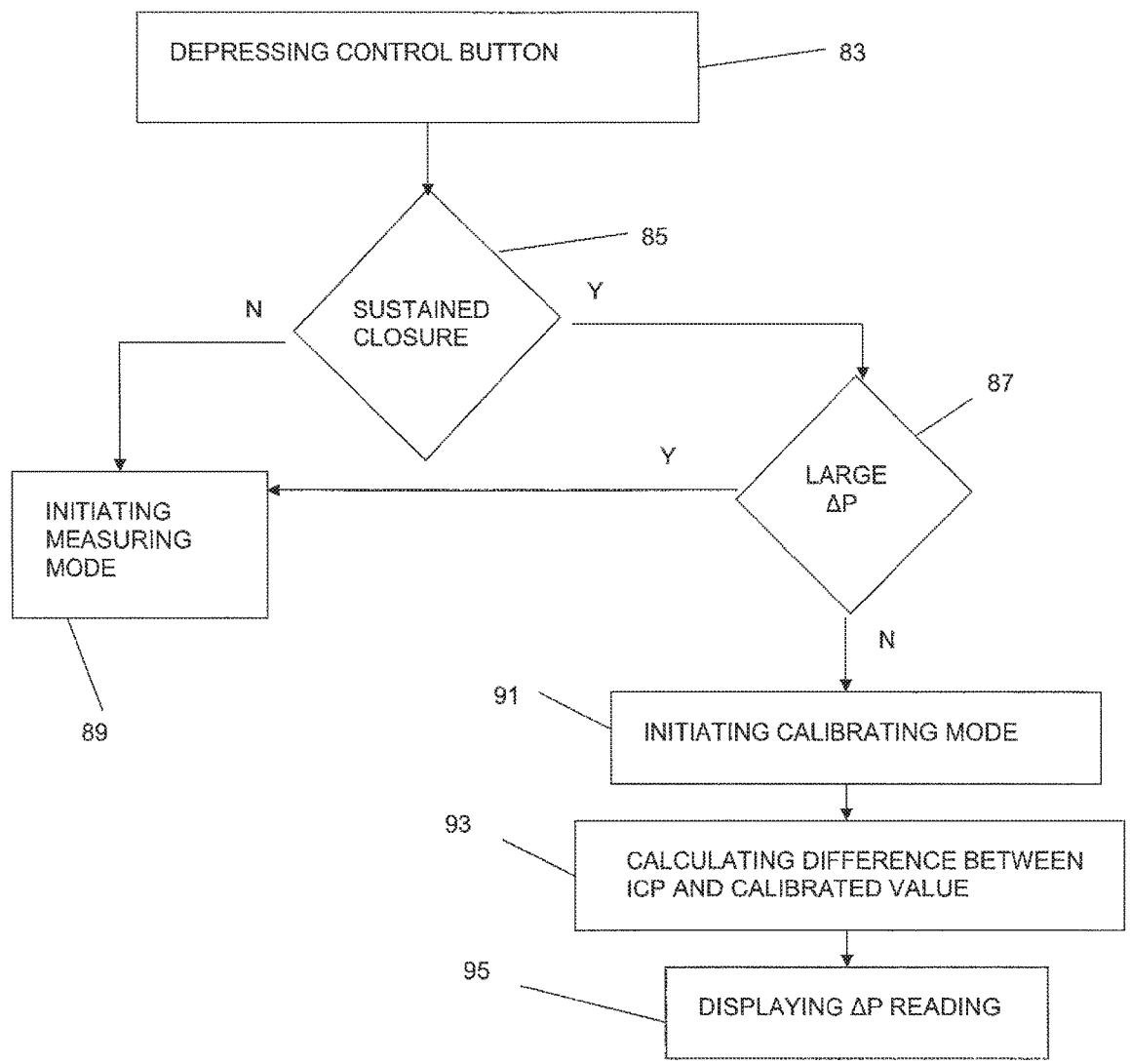
FIG. 7 is a method of operation during the calibrating mode.

FIG. 7 illustrates a method of operation during the calibrating mode. After the control button is depressed in step 83, the processor determines in step 85 whether the control button contact effects a sustained circuit closure. If it is determined that the control button contact effects a momentary closure, the pressure measuring mode is initiated in step 89. If, however, the control button contact effects a sustained closure, the processor then determines in step 87 whether the outputted differential pressure reading is greater than a predetermined value, e.g. 2 mmHg. If the differential pressure reading is greater than the predetermined value, indicating that a pressure reading is being performed, initiation of the calibrating mode is prevented and the differential pressure value is displayed. However, if the outputted differential pressure value is less than the predetermined value, the calibrating mode is initiated and the display is zeroed in step 91, thereby defining a calibrated ambient pressure. When a subsequent pressure reading is made, the processor computes the difference in step 93 between the pressure at the ICP port and calibrated ambient pressure, and outputs the value of the computed differential pressure reading in step 95 to the display.

After the desired ICP has been achieved, the plunger is secured to the barrel assembly, in order to facilitate monitoring of the ICP. FIGS. 8-12 illustrate one embodiment of means for securing the plunger to the barrel assembly. It will be appreciated, however, that other securing means are also within the scope of the invention.

Figure 8:
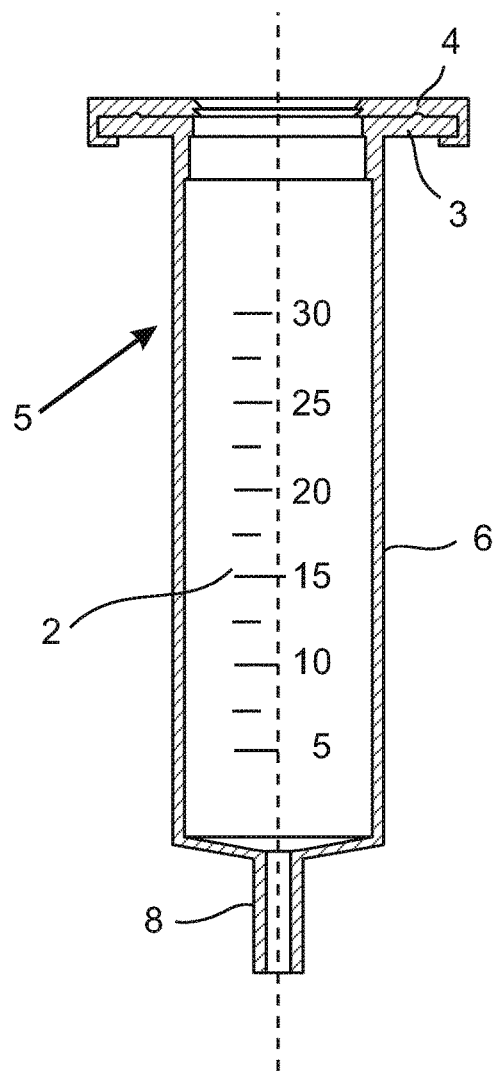
FIG. 8 is a front cross sectional view of a barrel assembly usable in conjunction with the syringe of FIG. 1.

FIG. 8 illustrates barrel assembly 5. Barrel assembly 5 comprises hollow barrel 6 provided with distal syringe tip 8 of a significantly smaller diameter than the diameter of barrel 6. A wing element 3 extends radially outwardly from the proximal end of barrel 6 and is engaged with upper locker ring 4. Visible graduated marks 2 are applied on barrel 6, to indicate to the clinician the volume of air that has been injected into the cuff.

Figure 9:
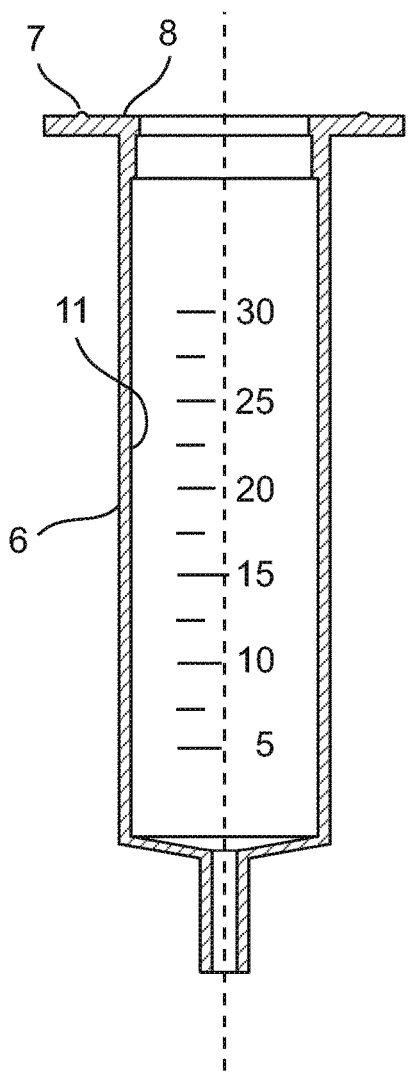
FIG. 9 is a front cross sectional view of the barrel assembly of FIG. 8, showing the wing element when separated from a locker ring.

As shown in FIG. 9, inner surface 8 of wing element 3 has a smaller diameter than the inner surface 11 of barrel 6. Two protuberances 7 for engaging the locker ring protrude upwardly from wing element 3.

Figure 10:
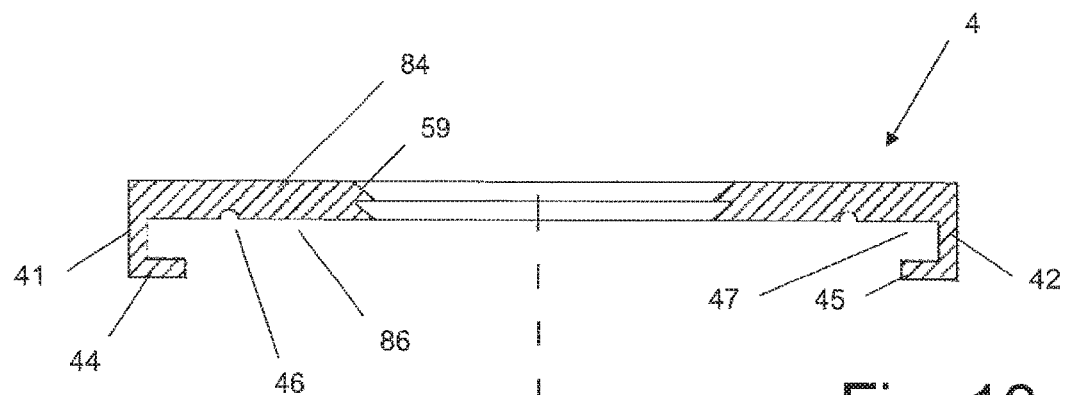
FIGS. 10 and 11 are front cross sectional and top views, respectively, of a locker ring.
Figure 11:
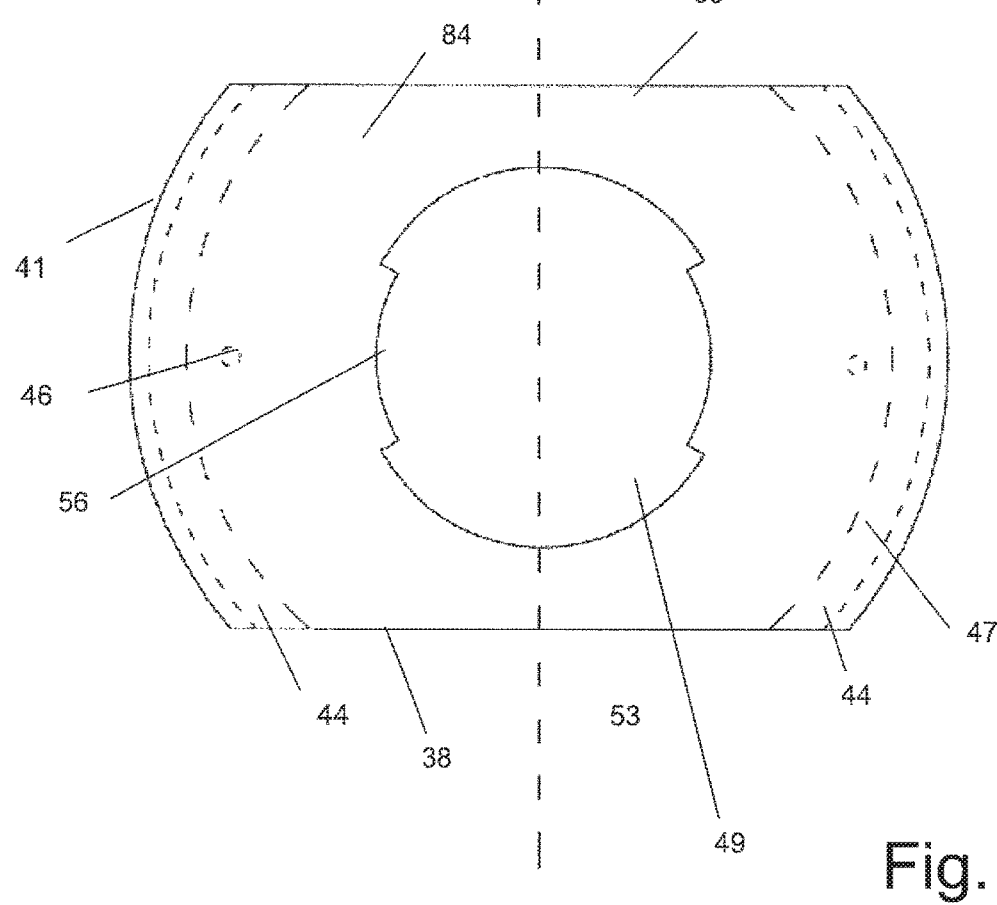

Locker ring 4 shown in FIGS. 10 and 11 has planar and mutually parallel upper and lower surfaces 84 and 86, which are defined by straight and mutually parallel front and rear edges 38 and 39 and by spaced convex side surfaces 41 and 42. Each of convex side surfaces 41 and 42 extend horizontally between front and rear edges 38 and 39 and extend downwardly from lower surface 86. A lip 44 which is parallel to lower surface 86 extends inwardly from the bottom of each side surface 41 and 42. Each of two end regions 13 of wing element 3 (FIG. 9) are receivable within the corresponding interspace 47 between lower surface 86 and lip 45. Two depressions 46, which are inwardly spaced from the inward edge 45 of lip 44 and alignable with the two protuberances 7 (FIG. 9), are formed in lower surface 86.

A central bore 49 is formed in locker ring 4. Bore 49 is defined by two spaced and concentric first circumferential edges 53 and 54 facing straight edges 38 and 39, respectively, and by two spaced and concentric second circumferential edges 56 and 57 facing convex side surfaces 41 and 42, respectively. The radius of each second circumferential edge is smaller than that of each first circumferential edge, and a radially oriented edge 59 downwardly extends from an end of a first circumferential edge to the closest end of a second circumferential edge.

Figures 12A, 12B, 12C:
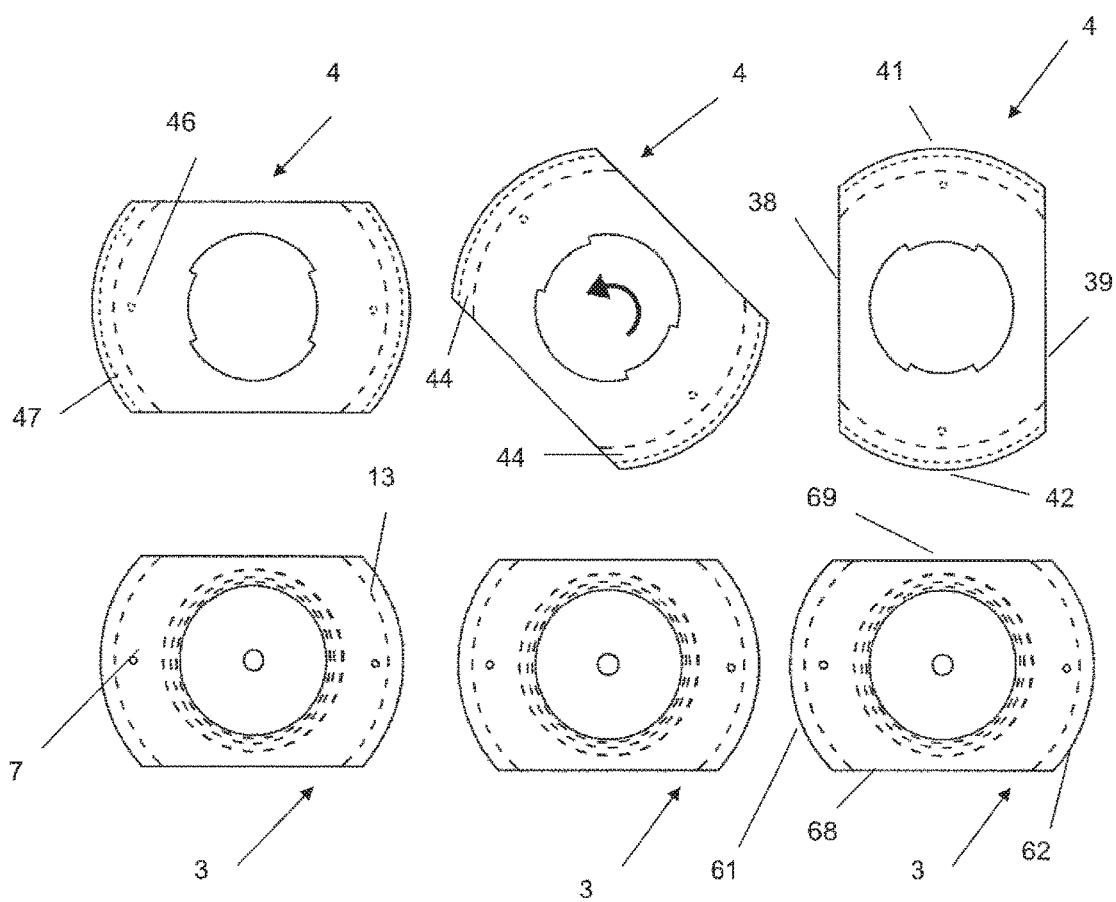
FIGS. 12A-C are a top view of the wing element of FIG. 9 and the locker ring of FIG. 11, showing three rotational positions, respectively of the locker ring when being engaged to the wing element.

Referring now to FIGS. 12A-C, wing element 3 is shown to have a similar shape as locker ring 4, being configured with straight and mutually parallel front and rear edges 68 and 69 and with spaced convex side surfaces 61 and 62. The spacing between straight edges 68 and 69 of wing element 3 is substantially equal to the spacing between straight edges 38 and 39 of locker ring 4, while the spacing between side surfaces 61 and 62 of wing element 3 is less than the spacing between side surfaces 41 and 42 of locker ring 4.

In order to have locker ring 4 engaged with wing element 3, the locker ring is first positioned above the wing element as shown in FIG. 12A such that the straight edges of locker ring 4 are substantially perpendicular to the straight edges of wing element 3. Locker ring 4 is then rotated as shown in FIG. 12B, while ensuring that one end of a lip 44 of locker ring 4 engages a corresponding side surface of wing element 3. After locker ring 4 is rotated 90 degrees, as shown in FIG. 12C, each protuberance 7 of wing element 3 is engaged with a corresponding depression 46 of locker ring 4 and each end region 13 of wing element 3 is received in a corresponding interspace 47 of locker ring 4.

Figure 13:
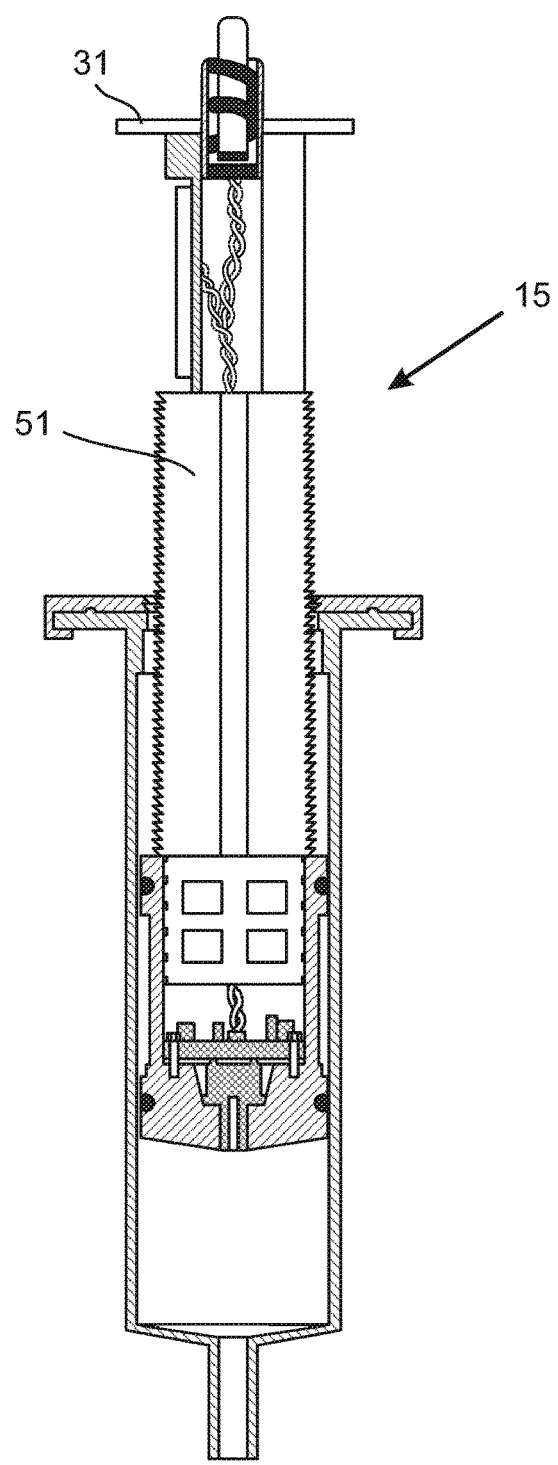
FIG. 13 is a side cross sectional view of the syringe of FIG. 1, showing the plunger being secured to the barrel assembly.

By virtue of the barrel assembly configuration, plunger 15 at one angular disposition is axially displaceable without resulting in interference between its tooth bearing member 51 and first circumferential edges 53 and 54 of locker ring 4 (FIG. 11). However, when flange 31 of plunger 15 is rotated to a second angular disposition, as shown in FIG. 13, tooth bearing member 51 becomes secured to a corresponding second circumferential edge 56 or 57 of locker ring 4 (FIG. 11) and the plunger is able to be retained at the selected axial position that generated a desired ICP without being dislodged therefrom. Plunger 15 nevertheless may be ratchedly displaced, if so desired, after having being secured to the barrel assembly.

When tooth bearing member 51 is becoming secured to locker ring 4 while plunger 15 is rotated, the axial displacement of the plunger resulting from the sliding action of the teeth along corresponding surfaces of the locker ring is insignificant and the discrepancy in measuring the barrel interior is negligible. The gap G between longitudinally spaced teeth 19 of tooth bearing member 51 (FIG. 2) is selected in order to ensure such an insignificant axial displacement of the plunger. For example for a syringe having an inner diameter of 20 mm, the longitudinal gap ranges from 0.5-1.5 mm, resulting in a discrepancy in measuring the barrel interior of only 0.16 mL.

Figure 14:
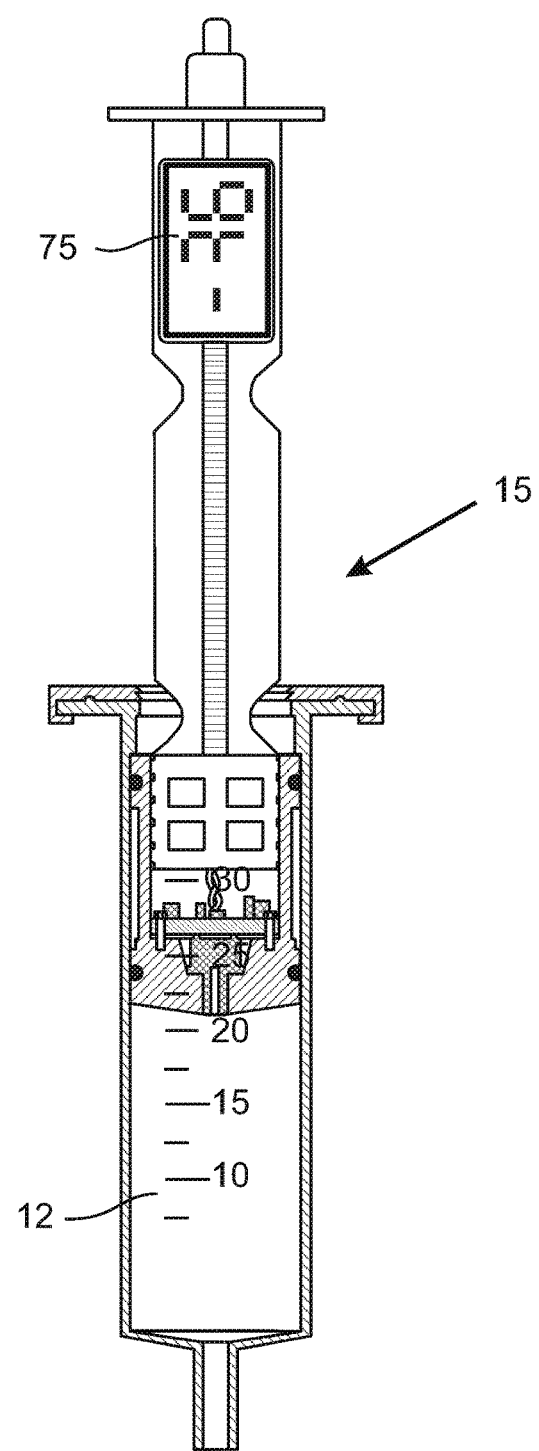
FIG. 14 is a front cross sectional view of the syringe of FIG. 1 when the plunger is proximally displaced to achieve a negative differential pressure reading.

While barrel interior 12 remains in fluid communication with the cuff, plunger 15 may be significantly proximally displaced, for example proximally displaced to a fullest extent as shown in FIG. 14, the displayed differential pressure reading 75 may be indicative of subatmospheric pressure, i.e. a negative displayed value of three indicia as shown. The ability to achieve subatmospheric pressure allows the cuff to be simply and quickly deflated.

The syringe of the present invention may also be used to draw accumulated liquid from a bodily lumen. A negative differential pressure may also be generated due to body resistance, enabling the body fluid to be drawn into barrel interior 12.

Figure 15:
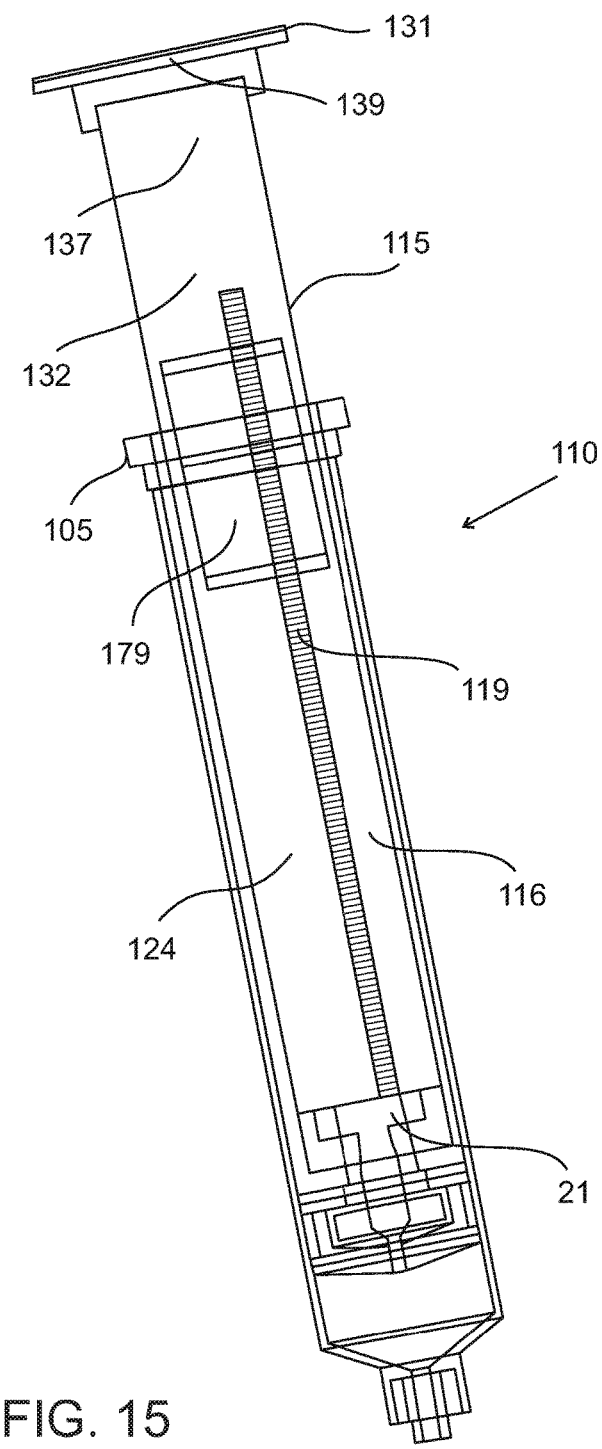
FIG. 15 is a perspective, partially removed view of a syringe according to another embodiment of the invention.
Figure 16:
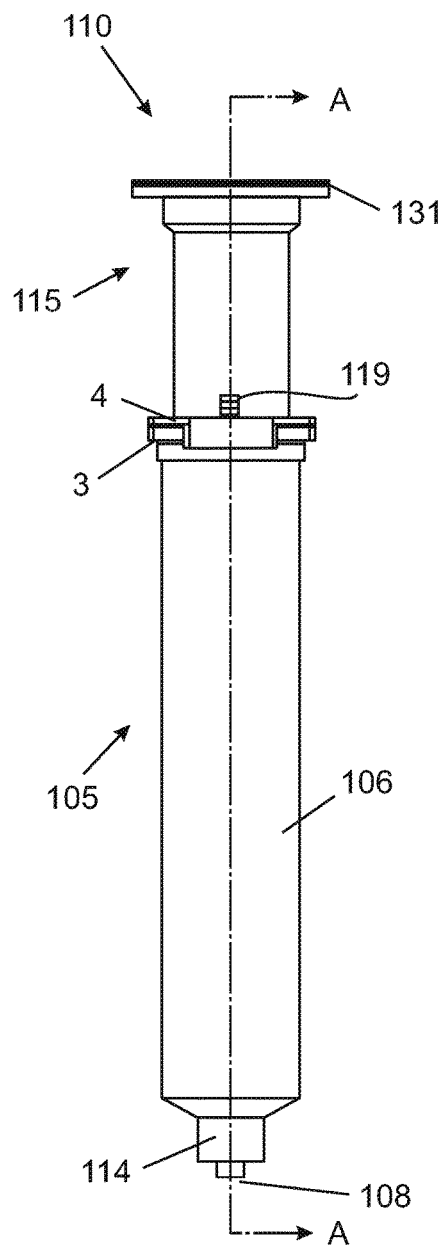
FIG. 16 is a front view of the syringe of FIG. 15.
Figure 17:
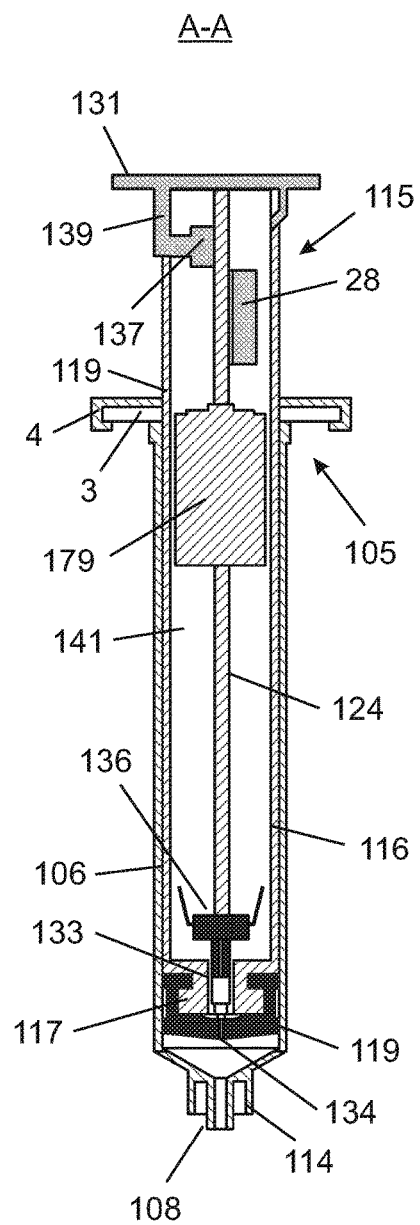
FIG. 17 is a cross sectional view of the syringe of FIG. 15, cut along plane A-A of FIG. 16.

Another embodiment of the invention is illustrated in FIGS. 15-17.

As shown in FIG. 15, syringe 110 comprises barrel assembly 105 and plunger 115. A printed circuit board (PCB) 124 comprising the amplifying and processing circuitry is housed within plunger 115, and extends from pressure sensor 21 to flange 131. PCB 124 may coincide with the longitudinal axis of plunger 115. Battery 179 is also housed within plunger 115, for example fitted within a central opening of PCB 124. Control button 137 is disposed substantially perpendicularly to PCB 124, and is accessible via an opening formed within a U-shaped housing member 139, which extends distally from flange 131 and protrudes outwardly from proximal end 132 of plunger 115. As control button 137 radially protrudes from the plunger body, plunger 115 will not be displaced when the control button is depressed. Display 28 (FIG. 17) is also housed within proximal end 132, being recessed at an opposite side to control button 137 while being visible. Sensor 21, display 28, control button 137, and battery 179 are all in electrical connection with PCB 124, and operate as described hereinabove in order to provide a differential pressure reading.

In this embodiment, longitudinally extending teeth elements 119 are integrally formed in one or more limited circumferential regions of the peripheral body 116 of plunger 115 in order to be temporarily secured to barrel assembly 105. An uppermost portion of a circumferential region is below display 28, and a lowermost portion thereof is above sensor 21. Rotation of flange 131 causes at least one region of teeth elements 119 to become secured to locker ring 4 of barrel assembly 105, allowing plunger 115 to be retained at a selected axial position that generated a desired ICP without being dislodged therefrom.

FIGS. 16 and 17 illustrate front and cross sectional views of syringe 110, respectively. Tubular engagement element 114 for engaging the tube surrounding the ETT valve distally extends from, and is of a smaller diameter than, barrel 106. Syringe tip 108 is of a smaller diameter than engagement element 114 and distally extends therefrom.

Distally and radially inwardly extending from cylindrical plunger body 117 is piston member 117. Gasket member 119 for sealingly engaging barrel 106 is coupled to a groove formed in piston member 117. A tubular sensor holder 133 for securing sensor 21 and passing through a central opening formed in piston member 117 is carried by gasket member 119. An annular piece 134 distally extending from, and having a diameter significantly less than, sensor holder 133 is fitted within gasket member 119, allowing ICP port 25 of sensor 21 to be in fluid communication with syringe tip 108. One or more ambient pressure ports 136 of pressure sensor 21 are radially spaced from PCB 179, so as to be exposed to the ambient pressure air flowing through the void regions 141 of plunger 115. It will be appreciated that syringe 10 of FIG. 1 may be configured with one or features of syringe 110, such as gasket member 119, PCB 124, a radially protruding control button 137, or an internally housed battery 179.

The analysis mode may be initiated by depressing the control button for a predetermined numbers of times, e.g. two, within a predetermined period of time, e.g. 3 seconds. During the analysis mode, the processor performs spectral analysis, or a predetermined frequency domain analysis, of the electrical signals that are generated in response to the pressure measurements. During the analysis mode, the processor may in a low power dormant state for a predetermined period of time and then be set to an active state in response to a wakeup event, such as when the ICP is greater than a predetermined threshold or less than a predetermined threshold, when the cuff inflate conduit is occluded, or after the predetermined period of time elapses in order to perform some measurements. In case of danger, a sound element may emit a blinking or buzzing sound.

Figure 19:
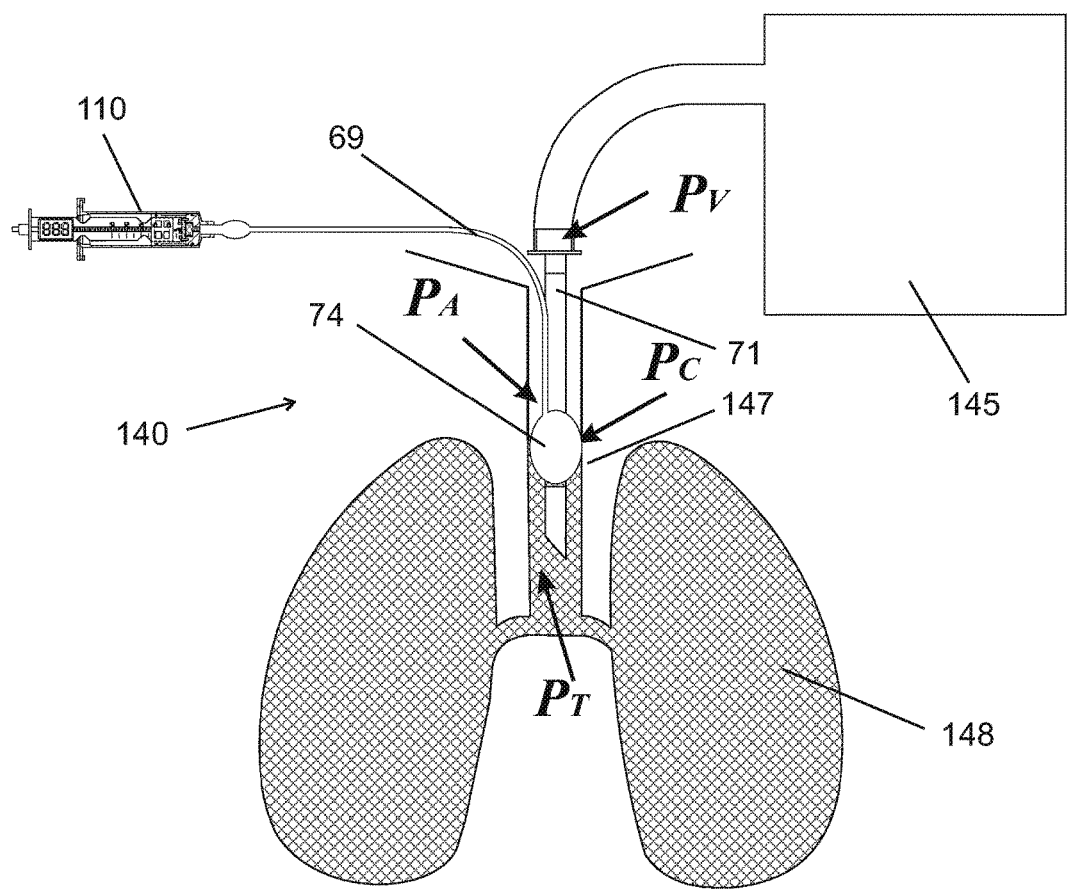
FIG. 19 is a schematic illustration of a respiration system with which the syringe of the present invention is operable.

FIG. 19 illustrates a typical respiration system 140 in conjunction with which syringe 110 is operable. Respiration system 140 comprises a ventilator 145 for delivering charges of air at pressure Pv via the main lumen of ETT 71 to trachea 147 and lungs 148, to assist a subject in breathing, achieving a tracheal pressure of $P_T$. Cuff 74 adapted to be in sealing relation with the tracheal wall is in fluid communication with the barrel interior of syringe 110 via conduit 69. The differential pressure sensor of syringe 110 measures the difference in pressure between ambient pressure $P_A$ and ICP $P_C$.

$P_C$ is varied in response to the change in $P_T$ due to inhalation and exhalation. At times, vapor from the airway infiltrates through the permeable cuff 74. The vapor condenses on ETT 71 due to the temperature differential between the relative high temperature of the vapor and the relative low temperature of the ETT. The condensed fluid droplets infiltrate and occlude conduit 69 for inflating cuff 74. A pressure reading of the ICP made via conduit 69 therefore reflects the pressure of air entrapped between valve 65 (FIG. 18) and the condensed droplets, and not of the actual ICP.

In contrast to the use of prior art devices by which the medical staff has been unable heretofore to determine whether a cuff is occluded, analysis of the generated signals by the processing circuitry of the present invention will easily indicate whether the cuff is occluded. Cuff 74 demonstrates good operability if the signal amplitude oscillates throughout a selected time duration. If, however, the amplitude remains substantially constant, it can be determined that the cuff inflate conduit is occluded, indicating that a maintenance procedure has to be performed. The degree of occlusion can also be determined by comparing an instantaneously received waveform with a stored waveform of normally oscillating signals. Analysis of the generated signals can also reveal that the cuff is ruptured when their amplitude remains at a constant value of zero and does not fluctuate in response to tracheal pressure $P_T$, even after performance of a maintenance procedure, generally distal displacement of the plunger to urge the condensed droplets into the cuff.

Figure 20:
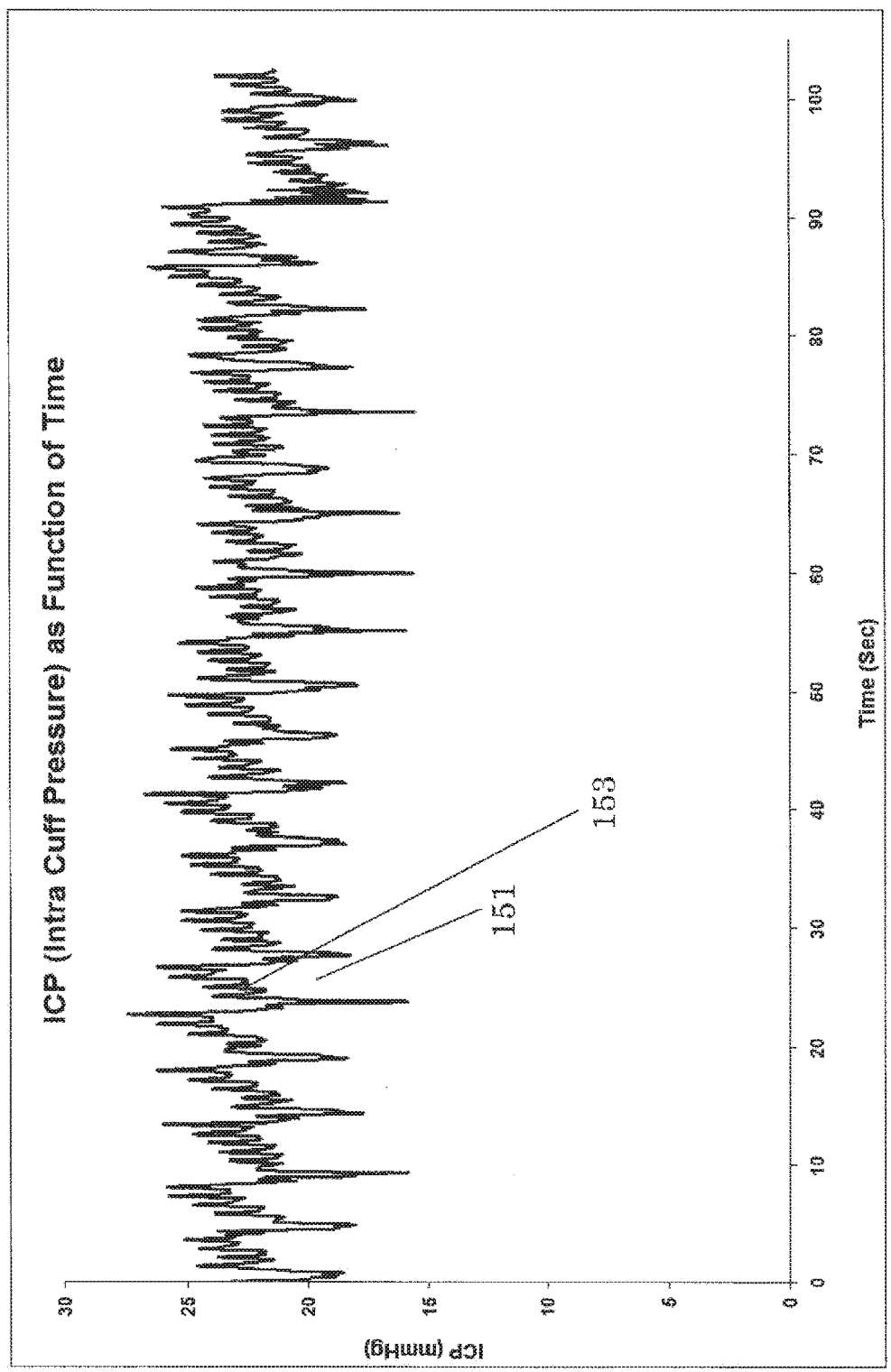
FIG. 20 is a graph of the ICP as a function of time.

As shown in FIG. 20, analysis of the generated signals can be used to detect the rate of breathing. By analyzing the ICP provided as a function of time, the rate of breathing, which directly influences the rate in change of the ICP, can also be determined. In the illustrated example whereby the data was sampled at rate of 20 Hz, the patient was found to breathe at a rate of 13 cycles per minute. Within each breathing cycle 151, a plurality of subcycles 153 having a smaller amplitude and duration and that modulate the main cycle 141 can be seen. Each subcycle 153 is representative of a portion of the blood pulse. Digital analysis of the blood pulse can be at times very helpful, for example to determine when a patient is suffering from high blood pressure, a condition that cannot always be determined by palpation.

Figure 21:
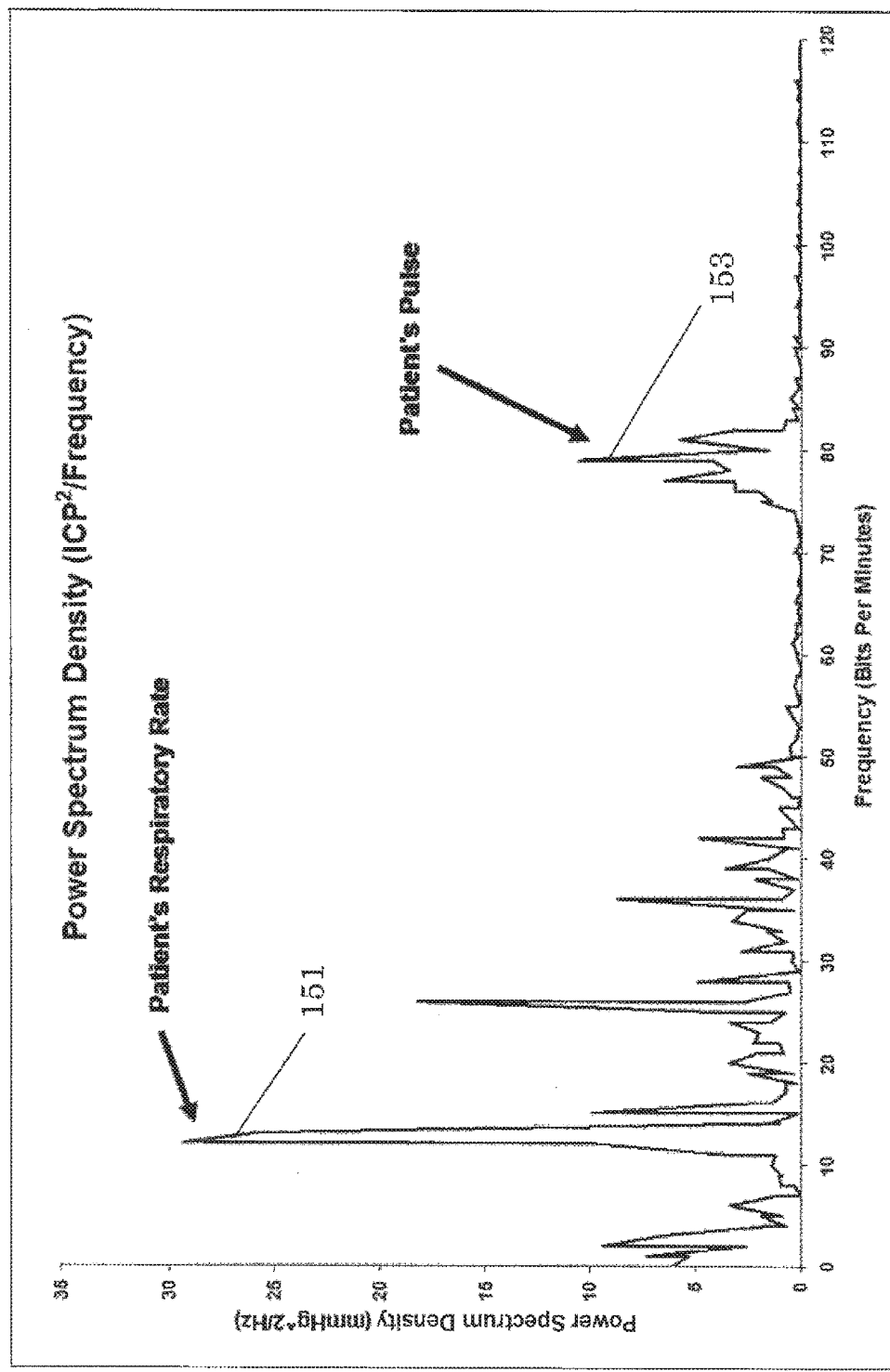
FIG. 21 is a graph of the power spectrum density of signals generated by the syringe of the present invention.

In the graph of power spectrum density shown in FIG. 21, an analysis of the generated signals can be performed by transforming the data from the time domain to the frequency domain by using Discrete Fourier Transform (DFT). The peaks generated in the time domain can be easily counted and thereby correlated with the peaks generated in the frequency domain. The breathing cycles 151 can be differentiated from the pulses 153 by a different characteristic bandwidth. The illustrated pulse is about 80 bits per minute.

Spectral analysis of the generated signals can also be very helpful, and even life saving, to patients requiring assisted ventilation due to non-synchronized breathing whereby the operation of ventilator 145 supplements the natural inhalation or exhalation of a patient. At times, according to prior art methods, the medical practitioner is unable to determine the current respiratory state, i.e. whether the patient is currently inhaling or exhaling. Consequently, the respiratory operation that the ventilator is performing may be detrimental or even contradictory to what the patient actually needs. In contrast, the present invention allows the medical practitioner to know the actual instant when a particular respiratory operation has to be initiated. Thus a medical practitioner manually operating a ventilator, such as one manufactured by Ambu A/S, Ballerup, Denmark, can synchronize an inhalation or exhalation step of the ventilator with a natural patient respiratory reflex.

The syringe of the present invention can be used to both measure and regulate the ICP for a cuff surrounding an ETT, a cuff surrounding a TRT, a cuff surrounding a laryngeal mask that is inserted into the pharynx for airway management, or a cuff for urine catheters.

Figure 22:
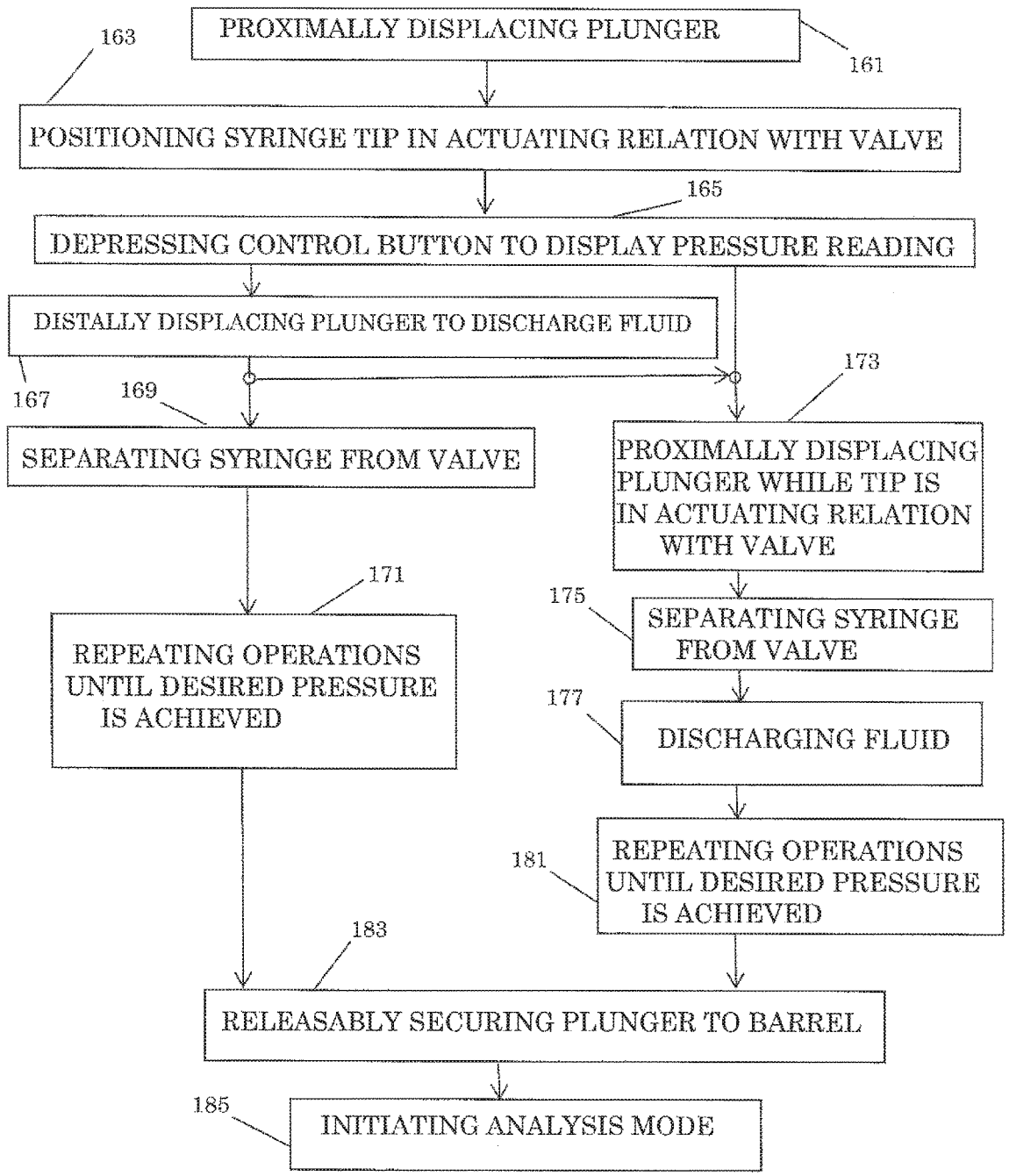
FIG. 22 is a flow chart of a method for regulating pressure in a fluid chamber.

As shown in FIG. 22, the pressure in a fluid chamber can be easily regulated by the syringe. The syringe plunger is first proximally displaced in step 161 to admit a charge of air into the barrel interior. The distal tip of the syringe is then sufficiently inserted in step 163 into a body enclosing a valve, e.g. a check or poppet valve, in fluid communication with the fluid chamber until the valve stem is actuated by the syringe tip. The control button is depressed in step 165 in order to perform pressure readings by means of the sensor throughout the pressure regulation procedure. The plunger is then distally displaced in step 167, causing the charge of air to be introduced into the fluid chamber and the instantaneous pressure within the fluid chamber to be displayed. If the pressure within the fluid chamber is less than a desired value, the syringe is separated from the valve in step 169, causing the valve element to return to its seat and to seal the fluid chamber. These operations are then repeated in step 171 until the desired pressure is achieved.

If the fluid chamber pressure is greater than the desired pressure, the plunger is proximally displaced in step 173 while the distal tip is in actuating relation with the valve. The syringe is separated from the valve in step 175 if the fluid chamber pressure is greater than the desired pressure and then the plunger is distally displaced in step 177 to discharge the received fluid. The distal tip is then brought again in actuating relation with the valve and the operations are repeated in step 181 until the desired pressure is achieved.

After the desired pressure has been achieved, the plunger is releasably secured to the barrel assembly in step 183 and then the analysis mode is initiated in step 185 by additionally depressing the control button.

Alternatively, the analysis mode may be initiated independently of pressure regulation process, for example at predetermined periods of time, after predetermined intervals, or according to the discretion of the medical staff. The analysis mode is generally initiated when the plunger is disposed at the distal end of the barrel and data is sampled for a predetermined duration, e.g. 1 minute.

The syringe may be used in life threatening situations to regulate the pressure in a cuff as described above, or for achieving hemostasis or for ensuring continuous vascular blood flow at a bleeding injury site of a wounded victim. Prior art methods involve using a tourniquet or the like to stop blood flow during cases of internal or external hemorrhage; however, a limb can develop gangrene if the blood flow is interrupted for a prolonged period of time of 4-6 hours. With use of the syringe of the present invention, pressurized fluid can be delivered to the injury site to stop the bleeding through the wounded blood vessel. The pressurized fluid is preferably applied, directly or by means of a cuffed medical tube, at less than the systolic pressure to ensure continuous blood flow through the wounded limb. The pressure of the applied fluid can be monitored or regulated by the syringe.

By monitoring and regulating the pressure of fluid administered into the blood stream or into organs, the pain normally accompanying such fluid transfer of patient having thin walled blood vessels can be advantageously alleviated.

The syringe may also be used to regulate the pressure in a fluid chamber not in contact with a human or animal bodily structure. For example, a bicycle tire may be inflated to a desired pressure when a syringe having a volume of 100 cc is employed, rather than using a conventional air pump whereby the inflated tire pump cannot be accurately determined.

The syringe may also be used to monitor the relative pressure of a bodily fluid chamber.

Injection of medication by a catheter primarily for purposes of analgesia into the epidural space located inside the spinal canal but outside the dura mater is a risky procedure since cerebrospinal fluid surrounding the spinal cord is located internally to the dura mater, and great care has to be taken to avoid puncturing the arachnoid layer containing the cerebrospinal fluid under pressure. The epidural space is characterized by subatmospheric pressure, and penetration into the epidural space can be positively identified by viewing the display. The syringe needle, which may have an axial opening or any other type of opening to enable fluid communication between the barrel interior and the epidural space, is slowly inserted through the vertebral bone until a rapid decrease in pressure indicative of penetration into the epidural space is noticed, whereupon the medication is injected. Prior art methods for identifying the epidural space by a reduction in resistance during introduction of the needle are less reliable.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

What is claimed is:

1. A pressure regulating syringe, comprising:
   a) a barrel assembly terminating with a tubular tip positionable in fluid communication with a fluid chamber;
   b) a plunger that is manually and axially displaceable within a barrel of said barrel assembly;
   c) a pressure sensor mounted onto said plunger adjacent to a distal end thereof, for generating one or more electrical signals representative of a differential pressure between a pressure in said fluid chamber and an ambient pressure;

d) circuitry housed within said plunger for processing said generated signals;

e) a control button configured for initiating a calibrating mode of said circuitry; and f) a display mounted on said plunger for displaying an output indicative of said processed signals, wherein said output is changeable upon axial displacement of said plunger when said tubular tip is positioned in fluid communication with said fluid chamber;

wherein said circuitry is configured to (i) prevent said calibrating mode and display said differential pressure when said differential pressure is greater than a predetermined value, and (ii) execute said calibrating mode for outputting a calibrated value of said ambient pressure to said display when said differential pressure is less than said predetermined value and when said barrel assembly tip is in fluid communication with an ambient pressure air.

2. The syringe according to claim 1, wherein the plunger comprises a distally disposed piston fitted with sealing means for sealingly engaging an inner surface of the barrel, said piston being formed with a central opening by which the pressure sensor is in fluid communication with the barrel assembly tip and the displayed output being a pressure reading.

3. The syringe according to claim 2, wherein the sensor is a differential pressure sensor having a first pressure port in fluid communication with the barrel assembly tip and a second pressure port in fluid communication with ambient pressure air flowing through a clearance between the plunger and the barrel assembly and through void regions of the plunger, the circuitry adapted to compute and to transmit to the display a pressure differential between the pressure of the fluid chamber and ambient pressure.

4. The syringe according to claim 3, wherein the ambient pressure is a calibrated value.

5. The syringe according to claim 3, wherein the differential pressure sensor is a piezoelectric pressure sensor.

6. The syringe according to claim 3, wherein the differential pressure sensor comprises two absolute pressure sensors configured such that the first pressure port is associated with a first absolute pressure sensor and the second pressure port exposed to ambient air is associated with a second absolute pressure sensor.

7. The syringe according to claim 2, wherein the plunger is axially displaceable to regulate the volume of a barrel interior between the sealing means and the barrel assembly tip and therefore the pressure of the fluid chamber, until a desired pressure reading is displayed.

8. The syringe according to claim 7, wherein the fluid chamber is a cuff surrounding a medical tube, said cuff being normally isolated from ambient pressure air by means of a valve and having a pressure that is regulatable during axial displacement of the plunger when the syringe is coupled to a connecting tube surrounding said valve and the barrel assembly tip actuates said valve.

9. The syringe according to claim 8, wherein the medical tube is selected from the group consisting of an endotracheal tube, a tracheotomy tube, a laryngeal mask airway tube, a cannula, and a catheter.

10. The syringe according to claim 1, wherein the control button is disposed on a proximal end of said plunger and is also configured for initiating a pressure measuring mode.

11. The syringe according to claim 1, wherein the plunger is releasably securable to the barrel assembly after a predetermined pressure differential reading is displayed.

12. The syringe according to claim 1, wherein the circuitry is operable in an analysis mode during which the generated signals are analyzed in a frequency or time domain.

13. The syringe according to claim 12, wherein the circuitry is set to a dormant state during operation of the analysis mode or of a pressure measuring mode and then set to an active state in response to a wakeup event.

14. A method for delivering pressurized fluid, comprising the steps of:

providing a syringe comprising a barrel assembly terminating with a tubular tip, a plunger that is axially displaceable within a barrel of said barrel assembly, a pressure sensor, mounted onto said plunger adjacent to a distal end thereof, circuitry housed within said plunger for processing said generated signals, a control button configured for initiating a calibrating mode of said circuitry, and a display mounted on said plunger for displaying an output indicative of said processed signals;

operating said control button to initiate said calibrating mode;

positioning said tip in fluid communication with a fluid chamber;

initiating a pressure measuring mode whereby said electrical signals being representative of a change in pressure within said fluid chamber are generated and an output associated with said signals is displayed on said display, and manually manipulating a fluid delivery element in response to said displayed output until a desired fluid delivery operation is performed;

wherein said pressure sensor generates electrical signals indicative of a differential pressure between a pressure in said fluid chamber and an ambient pressure; and wherein said circuitry is configured to (i) prevent said calibrating mode and display said differential pressure when said differential pressure is greater than a predetermined value, and (ii) execute said calibrating mode for outputting a calibrated value of said ambient pressure to said display when said differential pressure is less than said predetermined value and when said barrel assembly tip is in fluid communication with an ambient pressure air.

15. The method according to claim 14, wherein the displayed output is a pressure level in the fluid chamber.

16. The method according to claim 15, wherein the distal tip of the syringe is positioned in fluid communication with the fluid chamber by being placed in actuating relation with a valve which is in fluid communication with the fluid chamber and the plunger is manipulated in order to regulate the pressure in the fluid chamber.

17. The method according to claim 16, wherein the pressure in the fluid chamber is increased by proximally displacing the plunger to admit a charge of air into the barrel interior, placing the distal tip of the syringe in actuating relation with the valve, initiating a pressure adjustment mode by depressing a control button, distally displacing the plunger to cause said admitted charge of air to be discharged into the fluid chamber until a desired pressure reading is displayed, and separating the distal tip from the valve and repeating steps if the pressure within the fluid chamber is less than a desired value.

18. The method according to claim 17, wherein the pressure in the fluid chamber is decreased by proximally displacing the plunger while the distal tip is in actuating relation with the valve.

19. The method according to claim 17, further comprising the steps of releasably securing the plunger to the barrel after a desired pressure reading has been displayed and initiating an analysis mode by additionally depressing the control button.

20. The method according to claim 19, wherein an indication is provided in the analysis mode whether a cuff surrounding a medical tube is ruptured or whether a conduit for inflating said cuff is occluded.

21. The method according to claim 16, wherein the pressurized fluid is delivered to a cuff surrounding a medical tube, said medical tube being selected from the group consisting of an endotracheal tube, a tracheotomy tube, a laryngeal mask airway tube, a cannula, and a catheter.

22. The method according to claim 16, wherein the plunger is manipulated in order to inflate a tire.

23. The method according to claim 15, wherein the fluid chamber is the epidural space located within the spinal canal, and the epidural space is identified by securing a needle to the distal tip of the syringe and causing said needle to penetrate the vertebral bone until a decrease in pressure indicative of penetration into the epidural space is displayed, whereupon medication is injected into the epidural space via said needle.

24. The method according to claim 15, wherein the pressurized fluid is delivered to a bleeding injury site at less than the systolic pressure in order to stop a wounded blood vessel from bleeding.

25. The method according to claim 14, wherein the displayed output is a spectral analysis derived output of the generated signals.

26. The method according to claim 25, wherein the fluid delivery element is a ventilator and the spectral analysis output provides an indication of a current respiratory state of a patient suffering from non-synchronized breathing and requiring assisted ventilation.

* * * * *